(12) United States Patent
Bezencon et al.

(10) Patent No.: US 7,799,805 B2
(45) Date of Patent: Sep. 21, 2010

(54) PIPERIDINE CARBOXYLIC ACID AMIDE DERIVATIVES

(75) Inventors: Olivier Bezencon, Riehen (CH); Christoph Boss, Allschwil (CH); Daniel Bur, Allschwil (CH); Austin Chih-Yu Chen, Kirkland (CA); Olivier Corminboeuf, Allschwil (CH); Daniel Dube, Kirkland (CA); Walter Fischli, Allschwil (CH); Corinna Grisostomi, Allschwil (CH); Lubos Remen, Allschwil (CH); Sylvia Richard-Bildstein, Dietwiller (FR); Thierry Sifferlen, Guewenheim (FR); Michel Therien, Kirkland (CA); Thomas Weller, Binningen (CH)

(73) Assignee: Actelion Pharmaceuticals Ltd., Allschwil (CH)

(*) Notice: Subject to any disclaimer, the term of this patent is extended or adjusted under 35 U.S.C. 154(b) by 176 days.

(21) Appl. No.: 11/915,594

(22) PCT Filed: May 23, 2006

(86) PCT No.: PCT/IB2006/051641

§ 371 (c)(1),
(2), (4) Date: Nov. 27, 2007

(87) PCT Pub. No.: WO2006/129237

PCT Pub. Date: Dec. 7, 2006

(65) Prior Publication Data

US 2008/0214598 A1    Sep. 4, 2008

(30) Foreign Application Priority Data

May 27, 2005 (WO) ............... PCT/EP2005/005732
Jan. 13, 2006 (WO) ............... PCT/IB2006/050134

(51) Int. Cl.
*A01N 43/40* (2006.01)
*A61K 31/445* (2006.01)
*C07D 211/68* (2006.01)
*C07D 211/80* (2006.01)
*C07D 213/02* (2006.01)

(52) U.S. Cl. ...................... 514/318; 546/193

(58) Field of Classification Search .................. None
See application file for complete search history.

(56) References Cited

U.S. PATENT DOCUMENTS

| | | | |
|---|---|---|---|
| 5,175,179 A * | 12/1992 | Larson | ............ 514/369 |
| 5,380,758 A | 1/1995 | Stamler et al. | |
| 5,703,073 A | 12/1997 | Garvey et al. | |
| 5,994,294 A | 11/1999 | Garvey et al. | |
| 6,218,417 B1 | 4/2001 | del Soldato | |
| 6,242,432 B1 | 6/2001 | del Soldato | |
| 7,427,613 B2 | 9/2008 | Bezencon et al. | |

FOREIGN PATENT DOCUMENTS

| WO | WO 97/09311 | 3/1997 |
|---|---|---|
| WO | WO 98/19672 | 5/1998 |
| WO | WO00/64873 | 11/2000 |
| WO | WO00/64887 | 11/2000 |
| WO | WO 02/088101 | 11/2002 |
| WO | WO 03/093267 | 11/2003 |
| WO | WO 2004/002957 | 1/2004 |
| WO | WO 2004/089903 | 10/2004 |
| WO | WO2005/051911 | 6/2005 |
| WO | WO2005/061457 | 7/2005 |
| WO | WO2006/005741 | 1/2006 |
| WO | WO 2006/069788 | 7/2006 |
| WO | WO2006/103273 | 10/2006 |
| WO | WO2006/103275 | 10/2006 |
| WO | WO2006/103277 | 10/2006 |
| WO | WO2006/125621 | 11/2006 |

OTHER PUBLICATIONS

Waeber B. et al., "The renin-angiotensin system: . . . " Hypertension, Amsterdam, Elsevier Science Publishing Co., (1986), 489-519.
Weber, M.A., Am. J. Hypertens., (1992), 5, 247S.
Rosenberg, M.E., et al., Kidney International, (1994), 45, 403.
Breyer, J.A. et al., Kidney International, (1994), 45, S156).
Vaughan, D.E., et al., Cardiovasc. Res., (1994), 28, 159.
Fouad-Tarazi, F., et al., Am. J. Med., (1988), 84 (Suppl. 3A), 83) and myocardial infarction (Pfeffer M. A. et al., N. Engl. J. Med.), (1992), 327, 669.
Kleinert, H.D., Cardiovasc. Drugs, (1995), 9, 645.
Husain A., J. Hypertens., (1993), 11, 1155.
Israili, Z.H., et al., Annals of Internal Medicine, (1992), 117, 234.
Azizi, M. et al., J. Hypertens., (1994), 12, 419.
Neutel, J.M. et al., Am. Heart, (1991), 122, 1094.
Rahuel, J. et al., chem. Biol., (2000), 7, 493.
Mealy, N.E., Drugs of the Future, (2001), 26, 1139.
Oefner, C. et al., Chem. Biol., (1999), 6, 127.
Marki, H.P. et al., II Farmaco, (2001), 56, 21.
Int. J. Pharm. (1986), 33, 201-217.
Oae et al., Org. Prep. Proc. Int., 15(3): 165-198 (1983).
Mark Gibson, Editor, Pharmaceutical Preformulation and Formulation, IHS Health Group, Englewood, CO, USA, 2001.
Comins, D.L.; Brown, J.D., J. Org. Chem., (1989), 54, 3730.
Fischli, W. et al., Hypertension, (1991), 18:22-31.

(Continued)

*Primary Examiner*—James O Wilson
*Assistant Examiner*—Jeffrey H Murray
(74) *Attorney, Agent, or Firm*—Hoxie & Associates LLC

(57) ABSTRACT

The invention relates to novel piperidine carboxylic acid amide derivatives and their use as active ingredients in the preparation of pharmaceutical compositions. The invention also concerns related aspects including processes for the preparation of these novel compounds, pharmaceutical compositions comprising such compounds and especially the use of such compounds as inhibitors of renin.

9 Claims, No Drawings

OTHER PUBLICATIONS

Guller, R. et al., Bioorganic & Medicinal Chemistry Letters, vol. 9, No. 10, May 17, 1999, pp. 1403-1408.
U.S. Appl. No. 11/660,987, filed Dec. 10, 2009, Bezencon, et al.
U.S. Appl. No. 11/795,850, filed Jul. 3, 2008, Bezencon, et al.
U.S. Appl. No. 12/168,666, filed Dec. 18, 2008, Bezencon, et al.
U.S. Appl. No. 12/223,597, filed Jul. 9, 2009, Bezencon, et al.
U.S. Appl. No. 12/281,684, filed Mar. 5, 2009, Bezencon, et al.
Mark Gibson, Editor, Pharmaceutical Preformulation and Formulation, HIS Health Group, Englewood, CO, USA, 2001.
Remington, The Science and Practice of Pharmacy, $20^{th}$ Edition, Philadelphia College of Pharmacy and Science (2000).

* cited by examiner

PIPERIDINE CARBOXYLIC ACID AMIDE DERIVATIVES

This application is a U.S. filing under 35 U.S.C. 271 of PCT/IB2006/051641 filed on May 23, 2006, which claims the benefit of PCT/EP2005/005732, filed on May 27, 2005, and PCT/IB2006/050134 filed on Jan. 13, 2006, the contents of each of which are herein incorporated by reference. Novel compounds of the formula (I) are disclosed. Related aspects of this application include processes for the preparation of the compounds, pharmaceutical compositions comprising a compound of formula (I) and especially their use as renin inhibitors in cardiovascular events and renal insufficiency.

The invention relates to novel compounds of the formula (I). The invention also concerns related aspects including processes for the preparation of the compounds, pharmaceutical compositions comprising a compound of formula (I) and especially their use as renin inhibitors in cardiovascular events and renal insufficiency.

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (*Suppl. 3A*), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al., *Chem. Biol.*, 2000, 7, 493; Mealy N. E., *Drugs of the Future*, 2001, 26, 1139). Thus, renin inhibitors with good oral bioavailability and long duration of action are required. Recently, the first non-peptide renin inhibitors were described which show high in vitro activity (Oefner C. et al., *Chem. Biol.*, 1999, 6, 127; Patent Application WO 97/09311; Märki H. P. et al., *Il Farmaco*, 2001, 56, 21). However, the development status of these compounds is not known.

The present invention relates to renin inhibitors of a non-peptidic nature and of low molecular weight. Described are orally active renin inhibitors of formula (I) which have a long duration of action and which are active in indications beyond blood pressure regulation where the tissular renin-chymase system may be activated leading to pathophysiologically altered local functions such as renal, cardiac and vascular remodeling, atherosclerosis, and possibly restenosis. So, the present invention describes these non-peptidic renin inhibitors of formula (I).

In particular, the present invention relates to novel compounds of the formula (I)

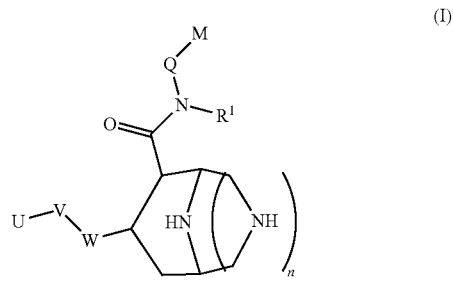

wherein

W is a phenyl ring or a six-membered, non benzofused aromatic ring containing one to four nitrogen atoms, wherein said rings are substituted by V in para position;

V represents a bond; —(CH$_2$)$_r$—; -A-(CH$_2$)$_s$—; —CH$_2$-A-(CH$_2$)$_t$—; —(CH$_2$)$_s$-A-; —(CH$_2$)$_2$-A-(CH$_2$)$_u$—; -A-(CH$_2$)$_v$—B—; —CH$_2$—CH$_2$—CH$_2$-A-CH$_2$—; -A-CH$_2$—CH$_2$—B—CH$_2$—; —CH$_2$-A-CH$_2$—CH$_2$—B—; —CH$_2$—CH$_2$—CH$_2$-A-CH$_2$—CH$_2$—; —CH$_2$—CH$_2$—CH$_2$—CH$_2$-A-CH$_2$—; -A-CH$_2$—CH$_2$—B—CH$_2$—CH$_2$—; —CH$_2$-A-CH$_2$—CH$_2$—CH$_2$—B—CH$_2$—; —CH$_2$-A-CH$_2$—CH$_2$—CH$_2$—; —CH$_2$—CH$_2$-A-CH$_2$—CH$_2$—B—; —O—CH$_2$—CH(OCH$_3$)—CH$_2$—O—; —O—CH$_2$—CH(CH$_3$)—CH$_2$—O—; —O—CH$_2$—CH(CF$_3$)—CH$_2$—O—; —O—CH$_2$—C(CH$_3$)$_2$—CH$_2$—O—; —O—CH$_2$—C(CH$_3$)$_2$—O—; —O—C(CH$_3$)$_2$—CH$_2$—O—; —O—CH$_2$—CH(CH$_3$)—O—; —O—CH(CH$_3$)—CH$_2$—O—; —O—CH$_2$—C(CH$_2$CH$_2$)—O—; or —O—C(CH$_2$CH$_2$)—CH$_2$—O—;

A and B independently represent —O— or —S—, preferably —O—;

U represents unsubstituted aryl; mono-, di-, tri- or tetra-substituted aryl wherein the substituents are independently selected from the group consisting of halogen, alkyl, alkoxy, and —CF$_3$; or mono-, di-, or tri-substituted heteroaryl wherein the substituents are independently selected from the group consisting of halogen, alkyl, alkoxy, and —CF$_3$;

Q represents methylene or ethylene, preferably methylene;

M represents an aryl, quinolinyl, isoquinolinyl, dihydroquinolinyl or tetrahydroquinolinyl group wherein said groups can optionally be mono- or di-substituted with substituents independently selected from the group consisting of alkyl; alkoxy; —OCF$_3$; —CF$_3$; hydroxy-alkyl; halogen; alkyl-O—(CH$_2$)$_{0-4}$—CH$_2$—; alkyl-O—(CH$_2$)$_{2-4}$—O—; R'$_2$N—(CH$_2$)$_{0-4}$—CH$_2$—, wherein R' is independently selected from the group consisting of hydrogen, alkyl (optionally substituted by one, two or three fluorine atoms), cyclopropyl, cyclopropyl-methyl, —C(=O)O—R'', and —C(=O)—R'' wherein R'' is C$_1$-C$_4$-alkyl, —CF$_3$, —CH$_2$—CF$_3$ or cyclopropyl; and R'''NH—C(=O)—(O)$_{0-1}$—(CH$_2$)$_{0-4}$—CH$_2$—, wherein R''' is alkyl or cyclopropyl;

R$^1$ represents alkyl or cycloalkyl, preferably cycloalkyl such as especially cyclopropyl;

n is the integer 0 or 1;

r is the integer 3, 4, 5, or 6;

s is the integer 2, 3, 4, or 5;

t is the integer 1, 2, 3, or 4;

u is the integer 1, 2, or 3; and v is the integer 2, 3, or 4;

and optically pure enantiomers, mixtures of enantiomers such as racemates, diastereomers, mixtures of diastereomers, diastereomeric racemates, mixtures of diastereomeric racemates, and meso-forms, as well as salts and solvates of such compounds, and morphological forms.

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference to a compound of formula (I) is to be understood as referring also to optically pure enantiomers, mixtures of enantiomers such as racemates, diastereomers, mixtures of diastereomers, diastereomeric racemates, mixtures of diastereomeric racemates, and meso-forms, as well as salts (especially pharmaceutically acceptable salts) and solvates (including hydrates) of such compounds, and morphological forms, as appropriate and expedient.

In the definitions of formula (I)—if not otherwise stated—the term alkyl, alone or in combination with other groups, means saturated, straight and branched chain groups with one to seven carbon atoms, preferably one to four carbon atoms, i.e. C$_1$-C$_4$-alkyl. Examples of alkyl groups are methyl, ethyl, n-propyl, iso-propyl, n-butyl, iso-butyl, sec-butyl, tert-butyl, pentyl, hexyl and heptyl. The methyl, ethyl and isopropyl groups are preferred.

The term alkoxy, alone or in combination with other groups, refers to an R—O— group, wherein R is an alkyl group. Examples of alkoxy groups are methoxy, ethoxy, propoxy, iso-propoxy, iso-butoxy, sec-butoxy and tert-butoxy.

The term hydroxy-alkyl, alone or in combination with other groups, refers to an HO—R— group, wherein R is an alkyl group. Examples of hydroxy-alkyl groups are HO—CH$_2$—, HO—CH$_2$CH$_2$—, HO—CH$_2$CH$_2$CH$_2$— and CH$_3$CH(OH)—.

The term halogen means fluorine, chlorine, bromine or iodine, preferably fluorine, chlorine or bromine, especially fluorine or chlorine.

The term cycloalkyl, alone or in combination, means a saturated cyclic hydrocarbon ring system with 3 to 7 carbon atoms, e.g. cyclopropyl, cyclobutyl, cyclopentyl, cyclohexyl and cycloheptyl. The cyclopropyl group is a preferred group.

The term aryl, alone or in combination, relates to a phenyl, naphthyl or indanyl group, preferably a phenyl group.

The term heteroaryl, alone or in combination, means six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing two heteroatoms independently selected from oxygen, nitrogen and sulfur and benzofused derivatives of such rings; five-membered aromatic rings containing three nitrogen atoms and benzofused derivatives thereof; a tetrazolyl ring; a thiazinyl ring; or coumarinyl. Examples of such ring systems are furanyl, thienyl, pyrrolyl, pyridinyl, pyrimidinyl, indolyl, quinolinyl, isoquinolinyl, imidazolyl, triazinyl, thiazolyl, isothiazolyl, pyridazinyl, pyrazolyl, oxazolyl, isoxazolyl, benzothienyl, quinazolinyl and quinoxalinyl.

Salts are preferably the pharmaceutically acceptable salts of the compounds of formula (I).

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

The compounds of the formula (I) may contain asymmetric carbon atoms and may be prepared in form of optically pure enantiomers, mixtures of enantiomers such as racemates, diastereomers, mixtures of diastereomers, diastereomeric racemates, mixtures of diastereomeric racemates, or mesoforms. The present invention encompasses all these forms. Mixtures are separated in a manner known per se, e.g. by column chromatography, thin layer chromatography (TLC), high performance liquid chromatography (HPLC), or crystallization.

Compounds of the invention also include nitrosated compounds of formula (I) that have been nitrosated through one or more sites such as oxygen (hydroxyl condensation), sulfur (sulfydryl condensation) and/or nitrogen. The nitrosated compounds of the present invention can be prepared using conventional methods known to one skilled in the art. For example, known methods for nitrosating compounds are described in U.S. Pat. Nos. 5,380,758, 5,703,073, 5,994,294, 6,242,432 and 6,218,417; WO 98/19672; and Oae et al., Org. Prep. Proc. Int., 15(3): 165-198 (1983).

A group of preferred compounds of formula (I) is that wherein n is the integer 1 and the ring substituents —CON(R$^1$)-Q-M and —W—V—U are trans to each other.

A group of especially preferred compounds of formula (I) is that wherein n is the integer 0 and the configurations at positions 3 and 4 of the piperidine ring of formula (I) are 3R and 4S, respectively.

A group of preferred compounds of formula (I) is that wherein M represents an aryl, quinolinyl, isoquinolinyl, dihydroquinolinyl or tetrahydroquinolinyl group wherein said groups can optionally be mono- or di-substituted with substituents independently selected from the group consisting of alkyl; alkoxy; —OCF₃; —CF₃; hydroxy-alkyl; halogen; alkyl-O—(CH₂)₀₋₄—CH₂—; alkyl-O—(CH₂)₂₋₄—O—; and R'₂N—(CH₂)₀₋₄—CH₂—, wherein R' is independently selected from the group consisting of hydrogen, alkyl, cyclopropyl, and —C(=O)—R" wherein R" is C₁-C₄-alkyl, —CF₃, —CH₂—CF₃ or cyclopropyl.

Another group of preferred compounds of formula (I) is that wherein M represents aryl, preferably phenyl, which is especially optionally mono- or di-substituted with substituents independently selected from the group consisting of alkyl, alkoxy, —OCF₃, —CF₃, hydroxy-alkyl and halogen, preferably from the group consisting of alkyl, alkoxy and halogen.

Another group of especially preferred compounds of formula (I) is that wherein M represents the following radical:

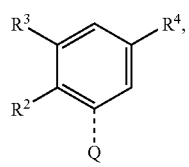

wherein R² is methyl or chlorine, R³ is hydrogen, and R⁴ is hydrogen, —CH₂CH₂—O—CH₃, —CH₂CH₂CH₂—O—CH₃, or R'NH—(CH₂)₀₋₁—CH₂—wherein R' is —CH₂—CHF₂, —CH₂—CF₃, cyclopropyl, —CO—CH₃, —CO—CH₂—CF₃, —CO—CH₂—CH₃, or cyclopropyl-carbonyl, with the proviso that in case R⁴ is hydrogen, R³ represents methyl, methoxy, chlorine, or —O—CH₂CH₂—O—CH₃.

A very preferred group of compounds of formula (I) is that wherein M represents the following radical:

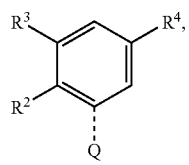

wherein R² is chlorine, R³ is hydrogen and R⁴ is —CH₂CH₂—O—CH₃.

A very preferred group of compounds of formula (I) is that wherein M represents the following radical:

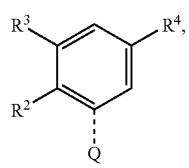

wherein R² is hydrogen, R³ is methoxyethoxy and R⁴ is

A further group of preferred compounds of formula (I) is that wherein Q is methylene.

A further group of preferred compounds of formula (I) is that wherein R¹ is cyclopropyl.

Another group of preferred compounds of formula (I) is that wherein W represents phenyl substituted by V in para position or the following radical:

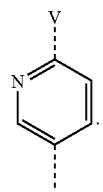

Another group of preferred compounds of formula (I) is that wherein W represents phenyl substituted by V in para position.

Another group of especially preferred compounds of formula (I) is that wherein W represents the following radical:

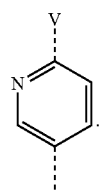

A further group of preferred compounds of formula (I) is that wherein V is —CH₂CH₂O— or —CH₂CH₂CH₂—, wherein in both cases the bivalent radical is linked to the group U of formula (I) via its oxygen atom, or —OCH₂CH₂O—.

A very preferred group of compounds of formula (I) is that wherein V represents —OCH₂CH₂O—.

Another group of preferred compounds of formula (I) is that wherein V is —OCH₂CH₂— or especially —CH₂CH₂CH₂O— [preferably wherein the —CH₂-part of —CH₂CH₂CH₂O— is linked to the group W of formula (I)].

A further group of preferred compounds of formula (I) is that wherein U is a mono-, di-, tri- or tetra-substituted aryl, preferably a mono-, di-, or tri-substituted phenyl, wherein the substituents are independently selected from the group consisting of halogen, alkyl, alkoxy, and —CF₃, especially from the group consisting of halogen and alkyl.

Another group of especially preferred compounds of formula (I) is that wherein U represents 2,6-dichloro-4-methylphenyl.

Another group of especially preferred compounds of formula (I) is that wherein U represents 2-chloro-3,6-difluorophenyl.

A preferred embodiment of the present invention relates to a compound of formula (I) wherein W represents phenyl substituted by V in para position or the following radical:

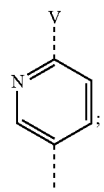

V represents —OCH₂CH₂O— or —CH₂CH₂CH₂O— wherein the —CH₂-part of —CH₂CH₂CH₂O— is linked to the group W of formula (I);

U represents tri-substituted phenyl wherein the substituents are independently selected from halogen (especially fluorine and chlorine) and alkyl (especially methyl);

Q represents methylene;

M represents the following radical:

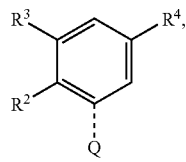

wherein $R^2$ is methyl or chlorine, $R^3$ is hydrogen, and $R^4$ is hydrogen, —CH$_2$CH$_2$—O—CH$_3$, —CH$_2$CH$_2$CH$_2$—O—CH$_3$, or R'NH—(CH$_2$)$_{0-1}$—CH$_2$— wherein R' is alkyl (optionally substituted by one or two fluorine atoms), cyclopropyl, cyclopropyl-methyl, —CO—CH$_3$, or —CO—CH$_2$—CF$_3$, with the proviso that in case $R^4$ is hydrogen, $R^3$ represents methyl, methoxy, or chlorine;

$R^1$ represents cyclopropyl; and n is the integer 0 or 1.

The present invention also relates to compounds of formula (I) wherein the meanings of one or more of the substituents and symbols as defined for formula (I), or a preferred embodiment of formula (I), are replaced by their preferred meanings as defined herein, such as those defined for the above-given preferred groups of compounds.

Especially preferred compounds of formula (I) are those selected from the group consisting of:

(1R*,5S*,6R*,7S*)-7-{4-[3-(2-chloro-3,6-difluoro-phenoxy)-propyl]-phenyl}-3,9-diaza-bicyclo[3.3.1]nonane-6-carboxylic acid cyclopropyl-(2,3-dichloro-benzyl)-amide, 4-{4-[3-(2-chloro-3,6-difluoro-phenoxy)-propyl]-phenyl}-piperidine-3-carboxylic acid cyclopropyl-(3-methoxy-2-methyl-benzyl)-amide, 4-{4-[3-(2,6-dichloro-4-methyl-phenoxy)-propyl]-phenyl}-piperidine-3-carboxylic acid cyclopropyl-(3-methoxy-2-methyl-benzyl)-amide, 4-{4-[3-(2,3,6-trifluoro-phenoxy)-propyl]-phenyl}-piperidine-3-carboxylic acid cyclopropyl-(3-methoxy-2-methyl-benzyl)-amide, 4-{4-[3-(2-chloro-3,6-difluoro-phenoxy)-propyl]-phenyl}-piperidine-3-carboxylic acid cyclopropyl-(2,3-dimethyl-benzyl)-amide, 4-{4-[3-(2,6-dichloro-4-methyl-phenoxy)-propyl]-phenyl}-piperidine-3-carboxylic acid cyclopropyl-(2,3-dimethyl-benzyl)-amide, 4-{4-[3-(2-chloro-6-fluoro-3-methyl-phenoxy)-propyl]-phenyl}-piperidine-3-carboxylic acid cyclopropyl-(2,3-dimethyl-benzyl)-amide, and 4-{4-[3-(2,3,6-trifluoro-phenoxy)-propyl]-phenyl}-piperidine-3-carboxylic acid cyclopropyl-(2,3-dimethyl-benzyl)-amide.

Further especially preferred compounds of formula (I) are those selected from the group consisting of:

(3R*,4S*)-4-{4-[2-(2,6-dichloro-4-methylphenoxy)ethoxy]phenyl}-piperidine-3-carboxylic acid cyclopropyl-(2,3-dimethylbenzyl)-amide, (3R,4S)-4-{4-[2-(2,6-dichloro-4-methyl-phenoxy)-ethoxy]-phenyl}-piperidine-3-carboxylic acid [2-chloro-5-(3-methoxy-propyl)-benzyl]-cyclopropyl-amide, (3R,4S)-4-{4-[2-(2,6-dichloro-4-methyl-phenoxy)-ethoxy]-phenyl}-piperidine-3-carboxylic acid [2-chloro-5-(2-methoxy-ethyl)-benzyl]-cyclopropyl-amide, (3R,4S)-6-[2-(2,6-dichloro-4-methyl-phenoxy)-ethoxy]-1',2',3',4',5',6',-hexahydro-[3,4']bipyridinyl-3'-carboxylic acid [2-chloro-5-(3-methoxy-propyl)-benzyl]-cyclopropyl-amide, and (3R,4S)-6-[2-(2,6-dichloro-4-methyl-phenoxy)-ethoxy]-1',2',3',4',5',6'-[3,4']bipyridinyl-3'-carboxylic acid [2-chloro-5-(2-methoxy-ethyl)-benzyl]-cyclopropyl-amide.

Another group of especially preferred compounds of formula (I) are those selected from the group consisting of:

(3R,4S)-4-{4-[2-(2,6-dichloro-4-methyl-phenoxy)-ethoxy]-phenyl}-piperidine-3-carboxylic acid {2-chloro-5-[(2,2-difluoro-ethylamino)-methyl]-benzyl}-cyclopropyl-amide, (3R,4S)-4-{4-[2-(2,6-dichloro-4-methyl-phenoxy)-ethoxy]-phenyl}-piperidine-3-carboxylic acid {2-chloro-5-[(3,3,3-trifluoro-propionylamino)-methyl]-benzyl}-cyclopropyl-amide, (3R,4S)-4-{4-[2-(2,6-dichloro-4-methyl-phenoxy)-ethoxy]-phenyl}-piperidine-3-carboxylic acid {2-chloro-5-[(cyclopropylmethyl-amino)-methyl]-benzyl}-cyclopropyl-amide, (3R,4S)-4-{4-[2-(2,6-dichloro-4-methyl-phenoxy)-ethoxy]-phenyl}-piperidine-3-carboxylic acid [5-(acetylamino-methyl)-2-chloro-benzyl]-cyclopropyl-amide, (3R,4S)-4-{4-[2-(2,6-dichloro-4-methyl-phenoxy)-ethoxy]-phenyl}-piperidine-3-carboxylic acid [2-chloro-5-(2-methylamino-ethyl)-benzyl]-cyclopropyl-amide, (3R,4S)-4-{4-[2-(2,6-dichloro-4-methyl-phenoxy)-ethoxy]-phenyl}-piperidine-3-carboxylic acid (2-chloro-5-methylaminomethyl-benzyl)-cyclopropyl-amide, (3R,4S)-4-{4-[2-(2,6-dichloro-4-methyl-phenoxy)-ethoxy]-phenyl}-piperidine-3-carboxylic acid {2-chloro-5-[2-(3,3,3-trifluoro-propionylamino)-ethyl]-benzyl}-cyclopropyl-amide, (3R,4S)-4-{4-[2-(2,6-dichloro-4-methyl-phenoxy)-ethoxy]-phenyl}-piperidine-3-carboxylic acid [2-chloro-5-(2-ethylamino-ethyl)-benzyl]-cyclopropyl-amide, (3R,4S)-4-{4-[2-(2,6-dichloro-4-methyl-phenoxy)-ethoxy]-phenyl}-piperidine-3-carboxylic acid [5-(2-acetylamino-ethyl)-2-chloro-benzyl]-cyclopropyl-amide, (3R,4S)-4-{4-[2-(2,6-dichloro-4-methyl-phenoxy)-ethoxy]-phenyl}-piperidine-3-carboxylic acid {2-chloro-5-[(2-fluoro-ethylamino)-methyl]-benzyl}-cyclopropyl-amide, (3R,4S)-4-{4-[2-(2,6-dichloro-4-methyl-phenoxy)-ethoxy]-phenyl}-piperidine-3-carboxylic acid (2-chloro-5-ethylaminomethyl-benzyl)-cyclopropyl-amide, (3R,4S)-4-{4-[2-(2,6-dichloro-4-methyl-phenoxy)-ethoxy]-phenyl}-piperidine-3-carboxylic acid (2-chloro-5-cyclopropylaminomethyl-benzyl)-cyclopropyl-amide, and (3R,4S)-4-{4-[2-(2,6-dichloro-4-methyl-phenoxy)-ethoxy]-phenyl}-piperidine-3-carboxylic acid [2-chloro-5-(2-cyclopropylamino-ethyl)-benzyl]-cyclopropyl-amide.

The compounds of formula (I) are useful for the treatment and/or prophylaxis of diseases such as or related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The compounds of formula (I) are especially useful for the treatment and/or prophylaxis of diseases such as or related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment or prophylaxis of diseases, which are associated with a dysregulation of the renin-angiotensin system, in particular to a method for the treatment or prophylaxis of the above-mentioned diseases, said methods comprising administering to a patient a pharmaceutically active amount of a compound of formula (I).

A further aspect of the present invention relates to pharmaceutical compositions comprising a compound of formula (I) and a pharmaceutically acceptable carrier material. These pharmaceutical compositions may be used for the treatment and/or prophylaxis of the above-mentioned diseases. The pharmaceutical compositions can be used for enteral, parenteral, or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The invention also relates to the use of a compound of formula (I) for the preparation of pharmaceutical compositions for the treatment or prophylaxis of the above-mentioned diseases.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Compounds of formula (I) or the above-mentioned pharmaceutical compositions are also of use in combination with other pharmacologically active compounds such as ACE-inhibitors, neutral endopeptidase inhibitors, aldosterone antagonists, angiotensin II receptor antagonists, endothelin receptors antagonists, vasodilators, calcium antagonists, potassium activators, diuretics, sympatholitics, beta-adrenergic antagonists, alpha-adrenergic antagonists and/or other drugs beneficial for the prevention or the treatment of the above-mentioned diseases such as 11beta-hydroxysteroid dehydrogenase type 1 inhibitors and soluble guanylate cyclase activators.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

Compounds of formula (I) can be prepared from a compound of type A (WO 03/093267; WO 04/002957) as described in Scheme 1, wherein W, V, U, and n are as defined for formula (I). PG stands for a suitable protecting group. $R^b$ stands for a suitable ester that can be cleaved later, for instance by saponification or hydrogenation. During the saponification of a compound of type A, a compound of type B is formed in 20-100% yield depending on the conditions, whereas the double bond has partially shifted to a deconjugated position. This compound may or may not be separated from the corresponding analogue with a double bond still conjugated, and an amide coupling for instance leads then to a compound of type C, wherein $R^1$, Q, and M are as defined for formula (I). During the amide coupling, by optimizing the conditions, the double bond can be shifted almost completely. A compound of type C is then reduced into a compound of type D. Finally, deprotection leads to a compound of formula (I). Of course the reduction can also happen on a compound of type B, which, in this case, is separated from its regioisomer with a still conjugated double bond. In this case a compound of type E is obtained, which is transformed into a compound of type D after amide coupling. If n=0, the conjugated compound of type A or B can be reduced to the corresponding saturated compound with magnesium in methanol. After equilibration the trans-configurated stereoisomer is isolated. Saponification (if necessary) leads to the compound of type E.

It will appear to the person skilled in the art that the sequence of these steps can be interverted or modified in most cases. The shift of the double bond in a compound of type B, and its reduction in compounds D and E, lead to mixtures of stereoisomers. These stereoisomers can be separated by standard methodologies, like flash column chromatography, HPLC, or chiral HPLC.

Scheme 1

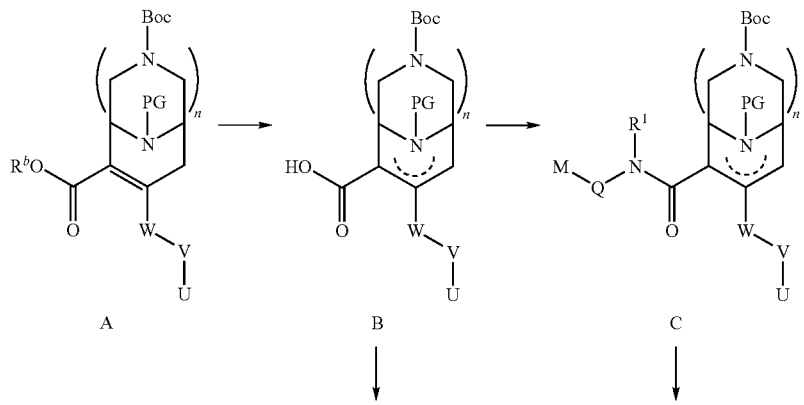

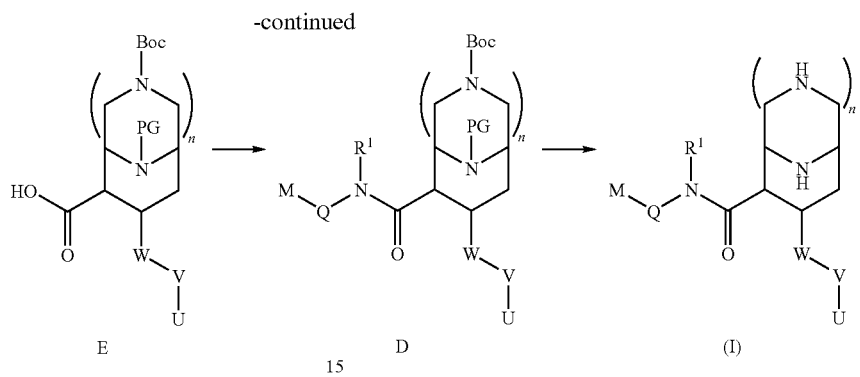

Otherwise a compound of type F can be used, as described in Scheme 2, wherein $R^b$ stands for a suitable ester substituent, and $R^a$ for a precursor of the substituent V as defined for formula (I). This compound of type F is transformed into a compound of type G, which in turn is transformed into a compound of type H, using amide coupling conditions that favor a shift of the double bond. Reduction of the double bond leads to a compound of type J, which is then transformed into a compound of formula (I). Also, a compound of type F can be reduced into a compound of type K. The U—V—W-chain is completed to yield a compound of type L, then the ester is hydrolysed to a compound of type E.

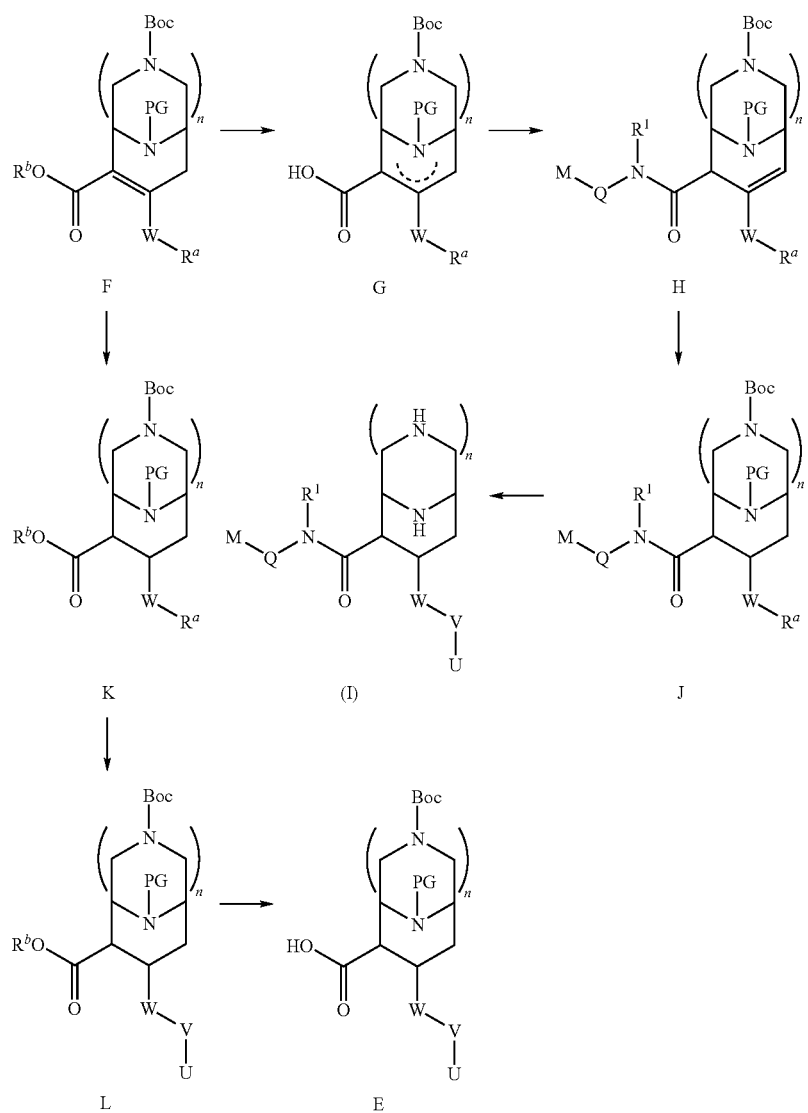

Scheme 2

EXAMPLES

| Abbreviations (as used herein): | |
|---|---|
| Ac | Acetyl |
| AcOH | Acetic Acid |
| Ang | Angiotensin |
| aq. | aqueous |
| 9-BBN | 9-Borabicyclo[3.3.1]nonane |
| Boc | tert-Butyloxycarbonyl |
| BSA | Bovine serum albumine |
| Bu | Butyl |
| BuLi | n-Butyllithium |
| conc. | Concentrated |
| Cy | Cyclohexyl |
| DIPEA | Diisopropylethylamine |
| DMAP | 4-N,N-Dimethylaminopyridine |
| DMF | N,N-Dimethylformamide |
| DMSO | Dimethylsulfoxide |
| EDC•HCl | Ethyl-N,N-dimethylaminopropylcarbodiimide hydrochloride |
| EIA | Enzyme immunoassay |
| ELSD | Evaporative Light Scattering Detection |
| eq. | Equivalent(s) |
| ES | Electrospray |
| Et | Ethyl |
| EtOAc | Ethyl acetate |
| EtOH | Ethanol |
| FC | Flash Chromatography |
| h | hour(s) |
| Hex | Hexane |
| HOBt | Hydroxybenzotriazol |
| HPLC | High Performance Liquid Chromatography |
| LC-MS | Liquid Chromatography - Mass Spectroscopy |
| Me | Methyl |
| MeOH | Methanol |
| min | minute(s) |
| MS | Mass Spectroscopy |
| NMO | N-methyl morpholine oxide |
| OAc | Acetate |
| OD | Optical density |
| org. | organic |
| PBS | Phosphate Buffered Saline |
| PG | protecting group |
| Ph | Phenyl |
| $R_f$ | Retention value (on TLC) |
| rt | room temperature |
| sat. | saturated |
| sol. | Solution |
| TBAC | Tetrabutylammonium chloride |
| TBAF | Tetrabutylammonium fluoride trihydrate |
| TBDMS | tert-Butyldimethylsilyl |
| TBTU | O-(benzotriazol-1-yl)-N,N,N',N'-tetramethyluronium tetrafluoroborate |
| tBu | tert-butyl |
| Tf | Trifluoromethylsulfonyl |
| TFA | Trifluoroacetic acid |
| THF | Tetrahydrofuran |
| TLC | Thin Layer Chromatography |
| $t_R$ | Retention time |
| UV | ultra violet |
| Vis | visible |

HPLC- or LC-MS-Conditions (if not Indicated Otherwise)

Analytic: Zorbax 59 SB Aqua column, 4.6×50 mm from Agilent Technologies.

Eluents: A: acetonitrile; B: $H_2O$+0.5% TFA. Gradient: 90% B→5% B over 2 min. Flow: 1 mL/min. Detection: UV/Vis+MS.

Preparative: Zorbax SB Aqua column, 20×500 mm from Agilent Technologies.

Eluent: A: Acetonitrile; B: $H_2O$+0.05% ammonium hydroxide (25% aq.). Gradient: 80% B→10% B over 6 min. Flow: 40 mL/min. Detection: UV+MS, or UV+ELSD.

Chiral, analytic: Regis Whelk column, 4.6×250 mm, 10 µm. Eluent A: EtOH+0.05% $Et_3N$. Eluent B: hexane. Isocratic conditions, 1 mL/min. The isocratic mixture may vary depending on the compounds.

Chiral, preparative: As analytical conditions, but on a Regis Whelk 01 column, 50×250 mm, flow at of 100 mL/min.

General Procedure for a Mitsunobu Coupling and a Boc-Deprotection

The desired phenol (2 eq.) is placed in a reaction flask. Compound J3 or J4 (about 80 mg, 1 eq.) dissolved in toluene (1 mL) is added, followed by the addition of azodicarboxylic dipiperidide (2 eq.) dissolved in toluene (1 mL). The reaction mixture is degassed with $N_2$ and finally $PBu_3$ (3 eq.) is added. The reaction is heated to 90° C. (on a pre-heated system) for 1 h, then cooled again to rt. $Et_2O$ (5 mL) is added, the mixture is filtered, and the solvents are evaporated under reduced pressure. The crude intermediate is purified by reversed phase HPLC. The clean product is dissolved in dioxane (1 mL), and HCl in dioxane (4M; 1 mL) is added. The mixture is stirred at rt for 2 h. The solvents are removed under reduced pressure to give the hydrochloride salt of final compound of formula (I).

General Conditions A for an Amide Coupling

HOBt (16.9 mg, 0.125 mmol), DMAP (3.05 mg, 0.025 mmol), DIPEA (0.068 mL, 0.40 mmol) and EDC.HCl (28.8 mg, 0.150 mmol) were added to a mixture of a carboxylic acid (0.100 mmol) and of an amine (0.100 mmol) in $CH_2Cl_2$ (1.00 mL). The mixture was stirred for 4 days at rt. The mixture was filtered through Isolute® (0.6 g of sorbent prepared with 1 mL aq. 1M HCl). The org. layer was evaporated under reduced pressure. The crude product was used further without purification.

General Conditions B for a Boc-Deprotection

The starting material was dissolved in $CH_2Cl_2$ (1 mL), and the sol. was cooled to 0° C. HCl (4M in dioxane, 0.5 mL), and the mixture was stirred for 1 h while warming up to rt. Aq. 1M NaOH was added, and the mixture was stirred further for 5 min. The layers were separated, and the org. layer was evaporated under reduced pressure. Purification by HPLC (acetonitrile with 0.05% aq. conc. $NH_3$/water 10:90→90:10 over an X-bridge column) yielded the title compound.

General Conditions C for an Amide Coupling Over the Acid Chloride

The starting carboxylic acid (1.00 eq.) was dissolved in toluene (14 mL/mmol of carboxylic acid), and DMF (catalytic amount) was added. Oxalyl chloride (1.30 eq.) was added, and the mixture was stirred for 1 h at rt. The solvents were removed under reduced pressure, and the crude acid chloride was divided in 0.100 mmol-portions of the following amide couplings. Such a portion of the acid chloride (0.100 mmol) was dissolved in $CH_2Cl_2$ (1.00 mL), and $Et_3N$ (0.014 mL, 0.10 mmol) and a sol. of the desired amine (0.100 mmol) in $CH_2Cl_2$ (0.50 mL) were added. The mixture was stirred for 1 h at rt, and was filtered through Isolute®, prewashed with aq. 1M HCl. After elution with $CH_2Cl_2$, the org. layer was evaporated under reduced pressure, and the residue was used in the next step without purification.

(rac.)-(1R*,5S*)-9-Methyl-7-trifluoromethanesulfonyloxy-3,9-diaza-bicyclo[3.3.1]non-6-ene-3,6-dicarboxylic acid 3-tert-butyl ester 6-ethyl ester (rac.)-(1R*,5S*)-9-Methyl-7-oxo-3,9-diaza-bicyclo[3.3.1]nonane-3,6-dicarboxylic acid 3-tert-butyl ester 6-ethyl ester (WO 2003/093267, 99.58 g, 305 mmol) is dissolved in dry THF (1450 mL) under a nitrogen atmosphere and the mixture is cooled to 0° C. NaH (16.64 g; 55% dispersion in mineral oil, 381 mmol) is added by portions of 2 g over a period of 35 min, keeping the temperature between 0 and 4° C. $H_2$ gas evolves. After the addition the mixture is yellow-green and is a slight suspension. The reaction mixture is stirred for 75 min at 0 to 4° C. Tf$_2$NPh (128.6 g, 360 mmol) is then added as a solid within 5 min. The reaction mixture becomes brown. The cooling bath is removed and the reaction is stirred over the weekend at rt. The reaction mixture is poured onto 1 L of ice/water and the solvents are removed under reduced pressure. The remaining water phase is extracted with (3×500 mL) EtOAc. The combined org. layers are washed with water (500 mL) and brine (500 mL). The org. phase is then dried over MgSO$_4$, filtered, and evaporated under reduced pressure. To the crude brown residue (174 g) is added 50 mL of pentane and the mixture is stirred at 4° C. overnight. The crystals are filtered off and washed with cold hexane (70 mL) and a cold mixture of hexane/Et$_2$O (4:1, 100 mL). This resulted in 84 g of product containing some TfNHPh. This material is filtered over silicagel (75 g). TfNHPh is washed out with CH$_2$Cl$_2$. This product is subsequently washed out with EtOAc (3 times 1 L) to give the title compound after evaporation under reduced pressure. The title compound is obtained in three fractions: a) 44.45 g of off-white crystals, b) 27.98 g of little brown crystals, and c) 15 g of a yellow oil containing the product and TfNHPh. After 2 days the TfNHPh contained in fractions c) crystallises. It is filtered to yield 9.43 g of the product as a brown oil.

Treatment of the Mother Liquors:

The combined mother liquors obtained above are concentrated under vacuo. The brown oil residue (75 g) is purified by FC (1500 g silica gel) using a gradient of (EtOAc/heptane 1-9→EtOAc). The column is then washed with EtOAc/MeOH 9:1. The title compound is isolated as 25.44 g of an off-white solid as the pure product. LC-MS: t$_R$=0.87 min; ES+: 459.24.

1-Allyl-4-bromo-benzene

Mg (8.76 g, 360 mmol) is suspended in THF (90 mL) under nitrogen in a three-necked flask equipped with a condenser and a dropping funnel. The dropping funnel is filled with 1,4-dibromobenzene (77.3 g, 327 mmol) in THF (40 mL). About 5% of the 1,4-dibromobenzene sol. is added carefully to the Mg-suspension and the reaction is started with the help of a heat gun. When the reaction starts, the 1,4-dibromobenzene sol. is added to such a speed so that the reaction mixture is refluxing gently (about 20 min). The mixture is stirred for further 30 min, and is cooled to 0° C. THF (100 mL) is added and the dropping funnel is filled with a sol. of allyl bromide (30.5 mL, 360 mmol) in THF (50 mL). The allyl bromide sol. is added slowly, maintaining the reaction temperature below 20° C. When the addition is complete, the mixture is stirred for further 30 min, while being cooled to 0° C. Aq. 1M HCl is added. The mixture is diluted with Et$_2$O, and washed with aq. 1M HCl and brine. The combined aq. extracts are extracted back with Et$_2$O. The combined org. extracts are dried over MgSO$_4$, filtered, and the solvents are removed under reduced pressure. Distillation of the residue (11 mbar, 88-92° C.) yields the title compound (39.3 g, about 61%), together with another, unidentified impurity.

3-(4-Bromo-phenyl)-propan-1-ol

BH$_3$ (1M in THF, 412 mL, 412 mmol) is added to a sol. of 1-allyl-4-bromo-benzene (204 g, 1.03 mmol) in THF (1.00 L) under nitrogen at 0° C. The mixture is stirred overnight while warming up to rt. Aq. NaOH (2.5M, 1.65 L, 4.12 mol) is added, and the mixture is cooled to 0° C. H$_2$O$_2$ (35%, 480 mL, 5.15 mol) is dropped carefully, and the mixture is stirred for 3 h. Et$_2$O is added, and the phases are separated. The org. layer is washed with water (1×), and brine (1×). The org. layer is dried over MgSO$_4$, filtered, and the solvents are removed under reduced pressure. Purification by FC (Et$_2$O/petroleum ether 1:1→Et$_2$O) yields the title compound (97.4 g, 44%).

[3-(4-Bromo-phenyl)-propoxy]-tert-butyl-dimethyl-silane

A sol. of 3-(4-bromo-phenyl)-propan-1-ol (49.4 g, 230 mmol) in DMF (500 mL) is cooled to 0° C., and imidazole (23.77 g, 349 mmol) and TBDMS-Cl (52.6 g, 349 mmol) are added. The mixture is stirred overnight, while warming up to rt. The mixture is diluted with heptane (1.0 L) and aq. sat. NH$_4$Cl (800 mL), and the mixture is shaken. The layers are separated. The aq. layer is extracted with heptane, and the combined org. extracts are washed with brine. The org. extracts are dried over MgSO$_4$, filtered, and the solvents are removed under reduced pressure. Purification by FC (Et$_2$O/heptane 1:99→1:19) yields the title compound (68.1 g, 90%). LC-MS: t$_R$=1.24 min.

2-(2,6-Dichloro-4-methyl-phenoxy)-ethanol

In a three-necked flask equipped with a gas droplet counter and an efficient cooling system, a mixture of 2,6-dichloro-p-cresol (20.0 g, 113 mmol), [1,3]dioxolan-2-one (9.95 g, 113 mmol) and imidazole (115 mg, 1.70 mmol) was heated to 160° C. for 25 h. The mixture was allowed to cool to rt. Purification by FC (Et$_2$O/heptane 1.1) yielded the title compound (18.7 g, 75%). LC-MS: t$_R$=0.88 min.

5-Bromo-2-[2-(2,6-dichloro-4-methyl-phenoxy)-ethoxy]-pyridine

A sol. of 2-(2,6-dichloro-4-methyl-phenoxy)-ethanol (18.6 g, 84 mmol) in THF (360 mL) was cooled to 0° C. NaH (about 55% in oil, 6.60 g, about 153 mmol) was added in portions, and the mixture was stirred at rt for 30 min. A sol. of 2,5-dibrompyridine (18.0 g, 76.3 mmol) in THF (60 mL) was added dropwise, and the mixture was heated to reflux for 90 min. The mixture was allowed to cool to rt, and ice was added carefully. The solvents were partially removed under reduced pressure, and the residue was diluted with EtOAc. This mixture was washed with aq. sat. NH$_4$Cl. The aq. layer was extracted back with EtOAc (2×). The combined org. extracts were washed with brine, dried over MgSO$_4$, filtered, and the solvents were removed under reduced pressure. Purification of the crude by FC (EtOAc/heptane 3:97) yielded the title compound (22.7 g, 79%). LC-MS: t$_R$=1.13 min; ES+: 378.08.

5-Bromo-2-chloro-N-cyclopropyl-benzamide

To a suspension of 5-bromo-2-chlorobenzoic acid (17.6 g, 75 mmol) in CH$_2$Cl$_2$ (180 mL) was added oxalyl chloride (7.0 mL, 83 mmol). DMF (8 drops) was added, and the mixture was stirred for 2 h at rt (gas evolution). The mixture was reduced under reduced pressure, and the crude residue was diluted with CH$_2$Cl$_2$ (530 mL). The mixture was cooled to 0° C., and a sol. of cyclopropylamine (5.8 mL, 83 mmol) in CH$_2$Cl$_2$ (45 mL) was added dropwise. The mixture was stirred for 10 min at 0° C., and was allowed to warm to rt. DIPEA (14.3 mL, 84 mmol) was added, and the mixture was stirred for 2 h at rt. The mixture was diluted with more CH$_2$Cl$_2$, and was washed with aq. 10% HCl, water, and brine. The org. layer was dried over MgSO$_4$, filtered, and the solvents were removed under reduced pressure. The residue was triturated with hexane, filtered, and dried under high vacuum to yield the title compound (19.3 g, 94%). LC-MS: t$_R$=0.84 min; ES+: 316.89.

2-Chloro-N-cyclopropyl-5-(3-methoxy-propenyl)-benzamide

5-Bromo-2-chloro-N-cyclopropyl-benzamide (19.3 g, 70.5 mmol) was dissolved in a mixture of DMF (350 mL) and 1-propanol (210 mL). Pd(OAc)$_2$(PPh$_3$)$_3$ (2.64 g, 3.53 mmol) was added. (E)-2-(3-Methoxypropenyl)4,4,5,5-tetramethyl-1,3,2-dioxaborolane (15 mL, 70.5 mmol) was added through a syringe, and aq. 2M Na$_2$CO$_3$ (123 mL) was added. The mixture was stirred at 80° C. for 2 h, and allowed to cool to rt. Aq. 10% HCl was added carefully until a pH of 2 was reached. The solvents were partially removed under reduced pressure, and the residue was extracted with Et$_2$O (3×). The combined org. extracts were washed with water and brine, dried over MgSO$_4$, filtered, and the solvents were removed under reduced pressure. Purification of the residue by FC (EtOAc/heptane 1:2→1:1→EtOAc) yielded the title compound (12.7 g, 68%). LC-MS: t$_R$=0.82 min; ES+: 266.17.

2-Chloro-N-cyclopropyl-5-(3-methoxy-propyl)-benzamide

2-Chloro-N-cyclopropyl-5-(3-methoxy-propenyl)-benzamide (12.6 g, 47.6 mmol) was dissolved in dry toluene (650 mL). Dry DMF (70 mL) was added, and the mixture was heated to 110° C. Benzensulfonyl hydrazine (24.5 g, 143 mmol) was added in three portions over 3 h. The mixture was heated for a total time of 3 h, and allowed to cool to rt. The solvents were removed under reduced pressure, and the residue was diluted with Et$_2$O. The mixture was washed with water, and the aq. phase was extracted back with Et$_2$O (3×). The combined org. extracts were washed with water, and brine, dried over MgSO$_4$, filtered, and the solvents were removed under reduced pressure. Purification of the residue by FC (EtOAc/heptane 1:9→1:4→1:3→1:1) yielded the title compound (10.0 g, 78%). LC-MS: t$_R$=0.83 min; ES+: 268.19.

[2-Chloro-5-(3-methoxy-propyl)-benzyl]-cyclopropyl-amine

LiAlH$_4$ (5.70 g, 151 mmol) was added in portions to a sol. of 2-chloro-N-cyclopropyl-5-(3-methoxy-propyl)-benzamide (10 g, 37.7 mmol) in THF (230 mL) at 0° C. The ice bath was removed, and the mixture was heated to reflux for 4 h. The mixture was allowed to cool to rt, and was cooled to 0° C. Water (7.5 mL), aq. 15% NaOH (17 mL), and water (5.7 mL) were carefully added. The mixture was filtered, and the precipitate was washed with EtOAc. The filtrate was evaporated under reduced pressure. The residue was diluted with EtOAc, and the resulting mixture was washed with water, and brine. The org. layer was dried over MgSO$_4$, filtered, and the solvents were removed under reduced pressure. Purification of the residue by FC (EtOAc/heptane 1:4→1:3→1:2) yielded the title compound (5.60 g, 59%). LC-MS: t$_R$=0.86 min; ES+: 254.19.

General Procedure for the Reductive Amination of Substituted Benzaldehydes with Cyclopropylamine:

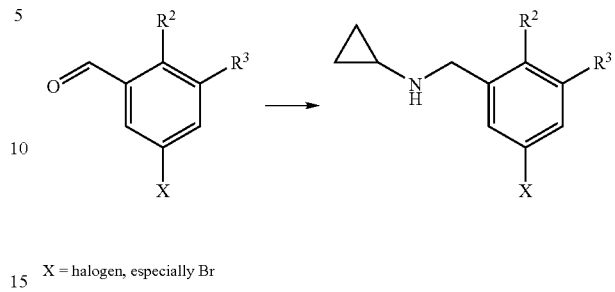

X = halogen, especially Br

A sol. of substituted benzaldehyde (17.8 mmol, 1.0 eq.), cyclopropylamine (3.13 mL, 44.5 mmol, 2.5 eq.) and sodium cyanoborohydride (1.34 g, 21.4 mmol, 1.2 eq.) in MeOH (100 mL) was treated with dropwise addition of glacial acetic acid (3.06 mL, 53.4 mmol, 3.0 eq.). The resulting sol. was stirred at rt for 16 h overnight. The reaction mixture was quenched with dropwise addition of sat. aq. NaHCO$_3$, and concentrated under reduced pressure to remove the MeOH. The crude residue was poured into a 250 mL separatory funnel containing sat. aq. NaHCO$_3$ (150 mL), and extracted with EtOAc (3×50 mL). The combined org. layers were washed with brine, dried over MgSO$_4$, filtered and concentrated under reduced pressure. Purification by FC yielded the benzamine product.

General Procedure for the Boc-Protection of Cyclopropyl-benzamines:

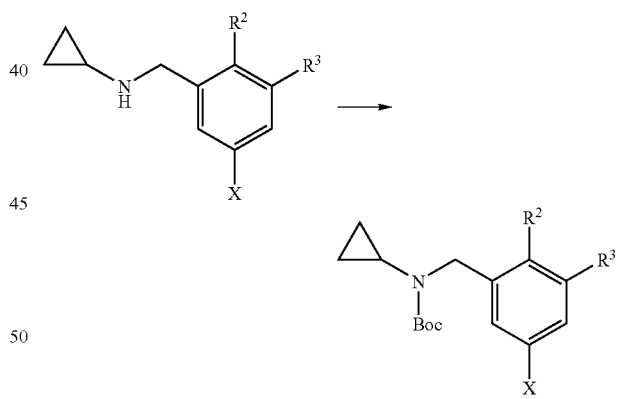

X = halogen, especially Br

A sol. of the cyclopropylbenzamine (43.7 mmol, 1.0 eq.) in a biphasic mixture of CH$_2$Cl$_2$ (50 mL) and 1M aq. NaOH (50 mL) was treated with Boc$_2$O (15.1 mL, 65.6 mmol, 1.5 eq.). The mixture was stirred at rt vigorously for 16 h. The mixture was poured into a 500 mL separatory funnel containing H$_2$O (300 mL), and extracted with CH$_2$Cl$_2$ (3×100 mL). The combined org. layers were washed with brine, dried over MgSO$_4$, filtered and concentrated under reduced pressure. Purification by FC yielded the Boc-protected amine.

General Procedure for the Allylation of Boc-Protected Cyclopropylbenzamines:

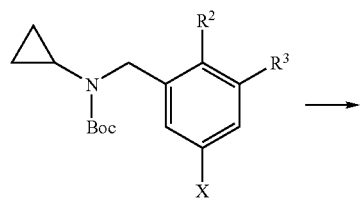

X = halogen, especially Br

Into a flame-dried round-bottom flask or Schlenk tube, under N₂ was added Pd[PCy₃]₂ (0.05 eq.), CsF (2.0 eq.) and the corresponding aryl bromide (1.0 eq.). If the aryl chloride was being used as a starting material, the (Pd[PtBu₃]Br)₂ dimer (0.025 eq.) was used in place of the Pd[PCy₃]₂ catalyst. The flask was evacuated under reduced pressure (0.1 mm Hg) and backfilled with N₂ (repeated 3 times). The resulting solids were dissolved in anhydrous THF or dioxane (0.15 M sol.) and tri-n-butyl allyltin (1.5 eq.) was added and the resulting mixture was refluxed for 8-16 h, until TLC shows complete consumption of starting material. The reaction mixture was cooled to rt, and filtered through a pad of silica gel on a sintered glass funnel, washing with Et₂O. The filtrate was concentrated and purified by FC to give the corresponding allylbenzamide derivative.

General Procedure for the Hydroboration/Oxidation of Allylbenzamines:

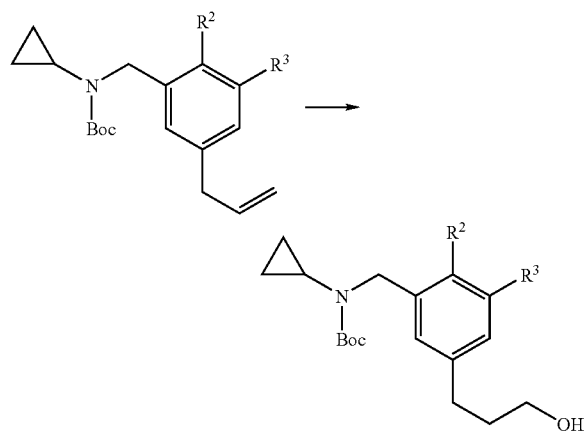

Into a flame-dried round-bottom flask equipped with a magnetic stir bar was added the allylbenzamine (1.0 eq.) and anhydrous THF (0.3 M sol.). The sol. was cooled to 0° C. and borane-dimethyl sulphide complex (1.1 eq.) was added dropwise over 20 min. The sol. was stirred at 0° C. for 1 h then allowed to warm to rt, and stirred for an additional 2 h. The sol. was cooled to 0° C. and 1M aq. NaOH was added dropwise (CAUTION—EXOTHERMIC REACTION) followed by dropwise addition of 30% aq. H₂O₂. The mixture was allowed to warm to rt, and stirred for 2 h. The mixture was poured into a separatory funnel containing H₂O and extracted with Et₂O (3 times). The combined org. layers were washed with brine, dried over MgSO₄, filtered and concentrated under reduced pressure. Purification by FC yielded the desired alcohol product.

General Procedure for the Oxidative Cleavage/Reduction of Allylbenzamines:

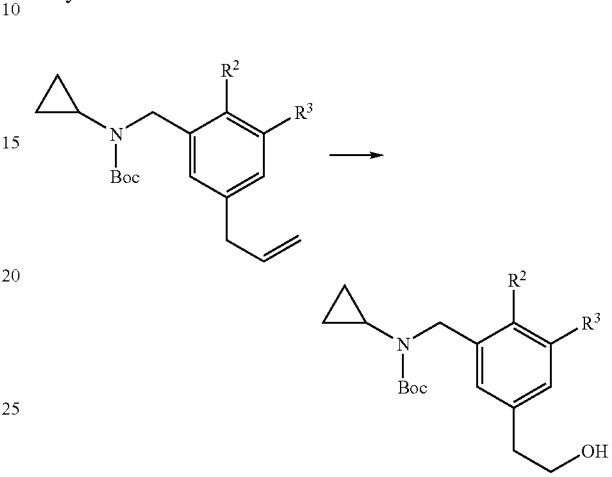

A sol. of allylbenzamine (1.0 eq.) in CH₂Cl₂ (0.4 M sol.) was cooled to −78° C. and O₃ gas was introduced into the sol. using a gas dispersion tube. The ozone gas was introduced until all of the starting material had been consumed, as determined by TLC, and the reaction mixture maintained a slight blue colour. The reaction was stirred at −78° C. for 20 min, then EtOH (0.5 M sol.) and NaBH₄ (2.5 eq.) were added. The mixture was allowed to warm to rt overnight (16 h). The reaction mixture was quenched with dropwise addition of sat. aq. NH₄Cl (5 mL), and poured into a separatory funnel containing sat. aq. NH₄Cl. The mixture was extracted with Et₂O (3 times). The combined org. layers were washed with brine, dried over MgSO₄, filtered and concentrated under reduced pressure. Purification by FC yielded the desired alcohol.

General Procedure for the Etherification of Aromatic Primary Alcohols with Methyl Iodide:

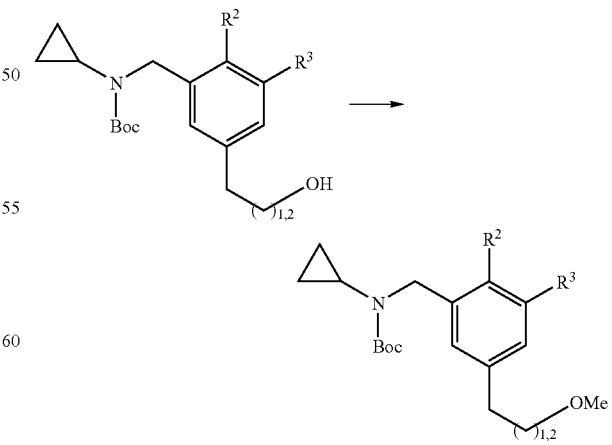

A suspension of the primary alcohol (1.0 eq.) in THF (0.25 M sol.) was cooled to 0° C. and treated with NaH (60% in oil, 2.0 eq.). The resulting mixture was stirred at 0° C. for 30 min and then at rt for another 30 min. The suspension was recooled to 0° C. and then MeI (8.0 eq.) was added in a single portion. The reaction mixture was stirred at 0° C. for 30 min, at rt for 30 min, and then heated to reflux for 4 h until all of the starting material was consumed as determined by TLC. The cooled reaction mixture was quenched with dropwise addition of sat. aq. NH$_4$Cl and poured into a separatory funnel containing sat. aq. NH$_4$Cl, and extracted with EtOAc (3 times). The combined org. layers were washed with brine, dried over MgSO$_4$, filtered and concentrated under reduced pressure. Purification by FC yielded the methyl ether.

General Procedure for the Deprotection of Boc-Protected Cyclopropylbenzamines:

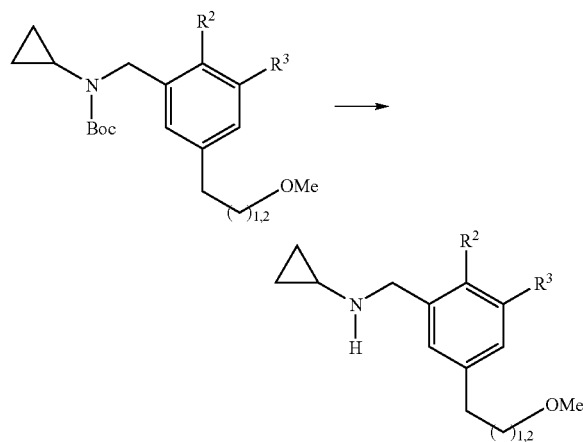

To a sol. of Boc-protected cyclopropylbenzamine (1.0 eq.) in CH$_2$Cl$_2$ (0.1-0.5 M sol.) was added 4 M HCl in dioxane (5.0 eq.). The resulting mixture was stirred at rt for 8-16 h until TLC shows complete conversion of starting material. The reaction was poured into a separatory funnel containing 1M aq. NaOH, and extracted with CH$_2$Cl$_2$ (3 times). Purification by FC yielded the corresponding free amine.

(5-Bromo-2-chloro-benzyloxy)-tert-butyl-dimethyl-silane

TBDMS-Cl (10.6 g, 66.7 mmol) was added to a sol. of (5-bromo-2-chloro-phenyl)-methanol (12.8 g, 55.6 mmol) and imidazole (9.42 g, 138 mmol) in DMF (190 mL) at 0° C. The mixture was stirred for 2 h at 0° C., and aq. sat. NH$_4$Cl was added. The mixture was extracted with heptane (2×). The combined org. extracts were dried over MgSO$_4$, filtered, and the solvents were removed under reduced pressure. Purification of the residue by FC (heptane→EtOAc/heptane 1:49) yielded the title compound (18.0 g, 96%). LC-MS: t$_R$=1.22 min.

3-(tert-Butyl-dimethyl-silanyloxymethyl)-4-chlorobenzaldehyde

BuLi (1.6M in hexane, 46.6 mL, 74.6 mmol) was added to a sol. of (5-bromo-2-chloro-benzyloxy)-tert-butyl-dimethyl-silane (16.7 g, 49.7 mmol) in THF (500 mL). The mixture was stirred for 30 min at −78° C., and DMF (19.2 mL, 249 mmol) was added at such a rate that the temperature did not raised above −70° C. The mixture was stirred for 30 min at −78° C., and was allowed to warm up to rt. The mixture was poured onto aq. sat. NH$_4$Cl. The resulting mixture was extracted several times with EtOAc. The combined org. extracts were dried over MgSO$_4$, filtered, and the solvents were removed under reduced pressure. Purification of the residue by FC (EtOAc/heptane 1:4) yielded the title compound (11.2 g, 79%). LC-MS: t$_R$=1.15 min.

[3-(tert-Butyl-dimethyl-silanyloxymethyl)-4-chloro-benzyl]-(2,2-difluoro-ethyl)-carbamic acid tert-butyl ester 2,2-Difluoroethylamine (660 mg, 7.90 mmol) was added to a sol. of 3-(tert-butyl-dimethyl-silanyloxymethyl)-4-chloro-benzaldehyde (1.50 g, 5.27 mmol) in MeOH (53 mL). The mixture was heated to reflux for 4 h, and was allowed to cool down to rt. NaBH$_4$ (300 mg, 7.90 mmol) was added carefully by portions, and the mixture was stirred for 1 h. The solvents were removed under reduced pressure, and the resulting oil was diluted with EtOAc. The mixture was washed with aq. sat. NaHCO$_3$ and brine. The org. layer was dried over MgSO$_4$, filtered, and the solvents were removed under reduced pressure to yield [3-(tert-butyl-dimethyl-silanyloxymethyl)-4-chloro-benzyl]-(2,2-difluoro-ethyl)-amine (1.86 g) as a clear crude oil that was used further directly. This crude material was dissolved in CH$_2$Cl$_2$ (53 mL), and DIPEA (2.7 mL, 15.6 mmol) was added, followed by Boc$_2$O (1.70 g, 7.90 mmol). The mixture was stirred at rt for 1 h. The mixture was diluted with CH$_2$Cl$_2$ (50 mL), and washed with aq. 1M HCl, aq. sat. NaHCO$_3$, and brine. The org. layer was dried over MgSO$_4$, filtered, and the solvents were removed under reduced pressure. Purification of the crude by FC (EtOAc/heptane 5:95) yielded the title compound (2.27 g, 96%). LC-MS: t$_R$=1.22 min.

(4-Chloro-3-hydroxymethyl-benzyl)-(2,2-difluoro-ethyl)-carbamic acid tert-butyl ester TBAF (1M in THF, 9.57 mL, 9.57 mmol) was added dropwise to a sol. of [3-(tert-butyl-dimethyl-silanyloxymethyl)-4-chloro-benzyl]-(2,2-difluoro-ethyl)-carbamic acid tert-butyl ester (2.15 g, 4.78 mmol) in THF (48 mL) at 0° C. The mixture was was stirred for 1 h while warming up to rt. The mixture was diluted with EtOAc, and the resulting mixture was washed with aq. sat. NH$_4$Cl (2×) and brine (1×). The org. layer was dried over MgSO$_4$, filtered, and the solvents were removed under reduced pressure. Purification of the crude by FC (EtOAc/heptane 30:70) yielded the title compound (591 mg, 37%). LC-MS: t$_R$=0.97 min; ES+: 336.09.

(4-Chloro-3-formyl-benzyl)-(2,2-difluoro-ethyl)-carbamic acid tert-butyl ester MnO$_2$ (830 mg, 8.59 mmol) was added to a sol. of (4-chloro-3-hydroxymethyl-benzyl)-(2,2-difluoro-ethyl)-carbamic acid tert-butyl ester (577 mg, 1.72 mmol) in CH$_3$CN (35 mL). The mixture was stirred at rt for 4.5 h, and MnO$_2$ (830 mg, 8.59 mmol) was added again. The mixture was stirred for 1 h. The mixture was filtered over Celite, and the precipitate was washed with CH$_3$CN and CH$_2$Cl$_2$. The filtrate was evaporated under reduced pressure to yield the crude title compound (563 mg, 98%) that was used further without purification. LC-MS: t$_R$=1.03 min.

(4-Chloro-3-cyclopropylaminomethyl-benzyl)-(2,2-difluoro-ethyl)-carbamic acid tert-butyl ester A mixture of (4-chloro-3-formyl-benzyl)-(2,2-difluoro-ethyl)-carbamic acid tert-butyl ester (563 mg, 1.69 mmol) and cyclopropylamine (0.180 mL, 2.52 mmol) in MeOH (18 mL) was heated to reflux for 4 h. The mixture was allowed to cool to rt. NaBH$_4$ (96 mg, 2.53 mmol) was added by portions, and the reaction was stirred for 1 h. The solvents were removed under reduced pressure, and the resulting oil was diluted with EtOAc. The mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 95:5) yielded the title compound (558 mg, 88%). LC-MS: t$_R$=0.76 min; ES+: 375.17.

3-(tert-Butyl-dimethyl-silanyloxymethyl)-4-chloro-benzaldehyde oxime 3-(tert-Butyl-dimethyl-silanyloxymethyl)-4-chloro-benzaldehyde (12.7 g, 44.6 mmol) was dissolved in CH$_3$CN (53 mL). To this sol. was added NaHCO$_3$ (11.2 g, 134 mmol), and the mixture was stirred vigorously for 5 min. Water (96 mL) was added and the mixture was stirred for 10 min. NH$_2$OH—HCl (6.20 g, 89.2 mmol) was added dropwise, followed by TBAC (622 mg, 2.24 mmol). The mixture was stirred at rt for 1 h, and AcOH (4.00 mL) was added dropwise to pH 6-7. The mixture was diluted with water (100 mL), and this mixture was extracted with Et$_2$O (3×). The combined org. extracts were dried over MgSO$_4$, filtered, and the solvents were removed under reduced pressure. Drying the residue under high vacuum yielded the crude title compound (15.1 g, 98%) that was used further without purification. LC-MS: t$_R$=1.09 min; ES+: 341.13.

3-(tert-Butyl-dimethyl-silanyloxymethyl)-4-chloro-benzylamine

LiAlH4 (4.11 g, 108 mmol) was added in portions to a sol. of 3-(tert-butyl-dimethyl-silanyloxymethyl)-4-chloro-benzaldehyde oxime (13.0 g, 43.4 mmol) in Et$_2$O (433 mL). The mixture was stirred for 1 h at rt. Aq. sat. potassium sodium tartrate (400 mL) was carefully added to the mixture. The mixture was stirred for 3 h, and was extracted with Et$_2$O (3×). The combined org. extracts were dried over MgSO$_4$, filtered, and the solvents were removed under reduced pressure. Drying under high vacuum yielded the crude title compound (12.4 g, quantitative yield) that was used further without purification. LC-MS: t$_R$=0.84 min; ES+: 327.37.

N-[3-(tert-Butyl-dimethyl-silanyloxymethyl)-4-chloro-benzyl]-3,3,3-trifluoro-propionamide TBTU (3.37 g, 10.5 mmol) was added to a sol. of 3-(tert-butyl-dimethyl-silanyloxymethyl)-4-chloro-benzylamine (2.00 g, 7.00 mmol), DIPEA (4.80 mL, 28.0 mmol) and 3,3,3-trifluoropropionic acid (0.927 mL, 10.5 mmol) in CH$_2$Cl$_2$ (70 mL). The mixture was stirred at rt for 1 h. CH$_2$Cl$_2$ (30 mL) was added, and the mixture was washed with aq. sat. NH$_4$Cl (2×), aq. 1M NaOH (1×) and brine (1×). The org. layer was dried over MgSO$_4$, filtered, and the solvents were removed under reduced pressure. Purification of the crude by FC (EtOAc/heptane 40:60) yielded the title compound (1.80 g, 65%). LC-MS: t$_R$=1.10 min; ES+: 396.15.

N-(4-Chloro-3-hydroxymethyl-benzyl)-3,3,3-trifluoro-propionamide

TBAF (1M in THF, 9.10 mL, 9.10 mmol) was added to a sol. of N-[3-(tert-butyl-dimethyl-silanyloxymethyl)-4-chloro-benzyl]-3,3,3-trifluoro-propionamide (1.80 g, 4.55 mmol) in THF (45 mL) at 0° C. The mixture was stirred for 1 h while warming up to rt. EtOAc (100 mL) was added, and the mixture was washed with aq. sat. NH$_4$Cl (3×) and water (4×). The org. layer was dried over MgSO$_4$, filtered, and the solvents were removed under reduced pressure. Purification of the crude by FC (EtOAc/heptane 70:30) yielded the title compound (835 mg, 65%). LC-MS: t$_R$=0.76 min; ES+: 323.02.

N-(4-Chloro-3-formyl-benzyl)-3,3,3-trifluoro-propionamide

MnO$_2$ (1.44 g, 14.9 mmol) was added to a sol. of N-(4-chloro-3-hydroxymethyl-benzyl)-3,3,3-trifluoro-propionamide (841 mg, 2.99 mmol) in CH$_3$CN (60 mL). The mixture was stirred at rt for 3 h. MnO$_2$ (1.44 g, 14.9 mmol) was added again, and the mixture was stirred for 90 min. The mixture was filtered over Celite, and the precipitate was washed with CH$_3$CN and CH$_2$Cl$_2$. The solvents were removed under reduced pressure, and the residue was dried under high vacuum, yielding the crude title compound (840 mg, quantitative yield) that was used without purification. LC-MS: t$_R$=0.84 min; ES+: 341.21.

N-(4-Chloro-3-cyclopropylaminomethyl-benzyl)-3,3,3-trifluoro-propionamide

A mixture of N-(4-chloro-3-formyl-benzyl)-3,3,3-trifluoro-propionamide (840 mg, 3.00 mmol) and cyclopropylamine (0.320 mL, 4.51 mmol) in MeOH (30 mL) was heated to reflux for 4 h. The mixture was allowed to cool to rt. NaBH$_4$ (170 mg, 4.51 mmol) was added in portions. The mixture was stirred for 1 h, and the solvents were removed under reduced pressure. The residue was diluted with EtOAc, and the resulting mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 90:10) yielded the title compound (929 mg, 96%). LC-MS: t$_R$=0.64 min; ES+: 321.05.

[3-(tert-Butyl-dimethyl-silanyloxymethyl)-4-chloro-benzyl]-cyclopropylmethyl-carbamic acid tert-butyl ester A mixture of 3-(tert-butyl-dimethyl-silanyloxymethyl)-4-chloro-benzylamine (2.00 g, 7.00 mmol) and cyclopropan-carboxaldehyde (0.784 mL, 10.5 mmol) in MeOH (70 mL) was heated to reflux for 4 h. The mixture allowed to cool to rt. NaBH$_4$ (397 mg, 10.5 mmol) was added in portion, and the mixture was stirred for 1 h at rt. The solvents were removed under reduced pressure, and the resulting oil was diluted with EtOAc. The resulting mixture was washed with aq. sat. NaHCO$_3$ and brine. The org. layer was dried over MgSO$_4$, filtered, and the solvents were removed under reduced pressure to yield the crude [3-(tert-butyl-dimethyl-silanyloxymethyl)-4-chloro-benzyl]-cyclopropylmethyl-amine. This crude product was dissolved in CH$_2$Cl$_2$ (70 mL). DIPEA (3.60 mL, 21.0 mmol) and Boc$_2$O (2.30 g, 10.5 mmol) were added. The mixture was stirred at rt for 2 h, and the mixture was diluted with CH$_2$Cl$_2$ (30 mL). The resulting mixture was washed with aq. 1M HCl, aq. sat. NaHCO$_3$, and brine. The org. layer was dried over MgSO$_4$, filtered, and the solvents were removed under reduced pressure. Purification of the crude by FC (heptane→EtOAc/heptane 10:90) yielded the title compound contaminated with Boc$_2$O (3.60 g, quantitative yield). LC-MS: t$_R$=1.25 min; ES+: 440.80.

(4-Chloro-3-hydroxymethyl-benzyl)-cyclopropylmethyl-carbamic acid tert-butyl ester TBAF (1M in THF, 14.0 mL, 14.0 mmol) was added to a sol. of [3-(tert-butyl-dimethyl-silanyloxymethyl)-4-chloro-benzyl]-cyclopropylmethyl-carbamic acid tert-butyl ester (3.08 g, 7.00 mmol) in THF (68 mL) at 0° C. The mixture was stirred for 1 h while warming up to rt. EtOAc was added, and the mixture was washed with aq. sat. $NH_4Cl$ and brine. The org. layer was dried over $MgSO_4$, filtered, and the solvents were removed under reduced pressure. Purification of the crude by FC ($CH_2Cl_2 \rightarrow CH_2Cl_2$/MeOH 9:1) yielded the title compound (1.00 g, 44%). LC-MS: $t_R$=0.99 min; ES+: 326.10.

(4-Chloro-3-formyl-benzyl)-cyclopropylmethyl-carbamic acid tert-butyl ester $MnO_2$ (1.48 g, 15.3 mmol) was added to a sol. of (4-chloro-3-hydroxymethyl-benzyl)-cyclopropylmethyl-carbamic acid tert-butyl ester (1.00 g, 3.07 mmol) in $CH_3CN$ (61 mL). The mixture was stirred at rt for 4 h, and $MnO_2$ (1.48 g, 15.3 mmol) was added again. The mixture was stirred for 1 h, and was filtered over Celite. The precipitate was washed with $CH_3CN$ and $CH_2Cl_2$. The filtrate was evaporated under reduced pressure. Drying the residue under high vacuum yielded the crude title compound (1.00 g, quantitative yield) that was used further without purification. LC-MS: $t_R$=1.06 min.

(4-Chloro-3-cyclopropylaminomethyl-benzyl)-cyclopropylmethyl-carbamic acid tert-butyl ester A mixture of (4-chloro-3-formyl-benzyl)-cyclopropylmethyl-carbamic acid tert-butyl ester (1.00 g, 3.09 mmol), $Et_3N$ (0.646 mL, 4.64 mmol) and cyclopropylamine (0.325 mL, 4.64 mmol) in MeOH (10.5 mL) was heated to reflux for 4 h. The mixture was allowed to cool to rt, and $NaBH_4$ (292 mg, 7.71 mmol) was added. The mixture was stirred for 1 h, and aq. sat. $NaHCO_3$ was added. The mixture was extracted with EtOAc (2×). The combined org. extracts were dried over $MgSO_4$, filtered, and the solvents were removed under reduced pressure. Purification of the crude by FC (MeOH/$CH_2Cl_2$ 1:49) yielded the title compound (535 mg, 48%). LC-MS: $t_R$=0.81 min; ES+: 406.20.

N-[3-(tert-Butyl-dimethyl-silanyloxymethyl)-4-chloro-benzyl]-acetamide

AcCl (0.547 mL, 7.70 mmol) was added to a sol. of 3-(tert-butyl-dimethyl-silanyloxymethyl)-4-chloro-benzylamine (2.00 g, 7.00 mmol) and DIPEA (4.80 mL, 28.0 mmol) in $CH_2Cl_2$ (70 mL) at 0° C. The mixture was stirred for 1 h while warming up to rt. $CH_2Cl_2$ (30 mL) was added, and the mixture was washed with aq. sat. $NH_4Cl$ (2×), aq. 1M NaOH (1×) and brine (1×). The org. layer was dried over $MgSO_4$, filtered, and the solvents were removed under reduced pressure. Purification of the crude by FC (EtOAc/heptane 60:40) yielded the title compound (2.10 g, 91%). LC-MS: $t_R$=1.07 min; ES+: 369.19.

N-(4-Chloro-3-hydroxymethyl-benzyl)-acetamide

TBAF (1M in THF, 12.0 mL, 12.0 mmol) was added to a sol. of N-[3-(tert-butyl-dimethyl-silanyloxymethyl)-4-chloro-benzyl]-acetamide (2.05 g, 6.00 mmol) in THF (60 mL) at 0° C. The mixture was stirred for 2 h while warming up to rt. EtOAc (100 mL) was added, and the mixture was washed with aq. sat. $NH_4Cl$ (1×) and water (4×1). The org. layer was dried over $MgSO_4$, filtered, and the solvents were removed under reduced pressure. Purification of the crude by FC ($CH_2Cl_2$/MeOH 90:10) yielded the title compound (750 mg, 59%). LC-MS: $t_R$=0.63 min; ES+: 237.09.

N-(4-Chloro-3-formyl-benzyl)-acetamide

NMO (1.15 g, 8.26 mmol) was added to a sol. of N-(4-chloro-3-hydroxymethyl-benzyl)-acetamide (588 mg, 2.75 mmol) in $CH_3CN$ (27 mL). The sol. was stirred for 30 min at rt, and tetrapropylammonium perruthenate (97 mg, 0.28 mmol) was added. The mixture was stirred for 1 h at rt, and was filtered over Celite. The precipitate was washed with $CH_3CN$. The filtrate was evaporated under reduced pressure. Purification of the crude by FC ($CH_2Cl_2$/MeOH 95:5) yielded the title compound (382 mg, 66%). LC-MS: $t_R$=0.71 min; ES+: 253.07.

N-(4-Chloro-3-cyclopropylaminomethyl-benzyl)-acetamide

A mixture of N-(4-chloro-3-formyl-benzyl)-acetamide (382 mg, 1.81 mmol) and cyclopropylamine (0.194 mL, 2.71 mmol) in MeOH (18 mL) was heated to reflux for 4 h. The mixture was allowed to cool to rt, and $NaBH_4$ (102 mg, 2.71 mmol) was added in portions. The mixture was stirred for 1 h, and the solvents were removed under reduced pressure. EtOAc (50 mL) was added, and the resulting mixture was washed with aq. sat. $NaHCO_3$ and brine. The org. layer was dried over $MgSO_4$, filtered, and the solvents were removed under reduced pressure. Purification of the crude by FC ($CH_2Cl_2$/MeOH 95:5) yielded the title compound (371 mg, 81%). LC-MS: $t_R$=0.53 min; ES+: 253.11.

tert-Butyl-[2-chloro-5-(2-nitro-vinyl)-benzyloxy]-dimethyl-silane

A mixture of 3-(tert-butyl-dimethyl-silanyloxymethyl)-4-chloro-benzaldehyde (14.0 g, 49.1 mmol) and ammonium acetate (3.79 g, 49.1 mmol) in nitromethane (8.19 mL, 152 mmol) and AcOH (39 mL) was heated to reflux for 3 h. The mixture was allowed to cool to rt, and was poured onto water. The resulting mixture was extracted several times with EtOAc. The combined org. extracts were washed with water and aq. sat. $NaHCO_3$ several times. The org. layer was dried over $MgSO_4$, filtered, and the solvents were removed under reduced pressure. The residue was dried under high vacuum overnight, and was dissolved in DMF (217 mL). The sol. was cooled to 0° C., and imidazole (8.36 g, 123 mmol) and TBDMS-Cl (8.84 g, 58.6 mmol) were added. The mixture was stirred for 2 h at 0° C., and was poured onto aq. sat. $NH_4Cl$. The resulting mixture was extracted with EtOAc several times. The combined org. extracts were washed with water and brine. The org. layer was dried over $MgSO_4$, filtered, and the solvents were removed under reduced pressure. Purification of the crude by FC (EtOAc/heptane 2:8) yielded the title compound (9.50 g, 59%). LC-MS: $t_R$=1.18 min.

2-[3-(tert-Butyl-dimethyl-silanyloxymethyl)-4-chloro-phenyl]-ethylamine $LiAlH_4$ (1.09 g, 28.7 mmol) was added to a sol. of tert-butyl-[2-chloro-5-(2-nitro-vinyl)-benzyloxy]-dimethyl-silane (3.95 g, 11.5 mmol) in $Et_2O$ (115 mL). The mixture was stirred for 1 h at rt, and aq. sat. potassium sodium tartrate was added. The mixture was stirred for 1 h, and the layers were separated. The aq. layer was extracted several times with $Et_2O$. The combined org. extracts were dried over $MgSO_4$, filtered, and the solvents were removed under reduced pressure. Drying the residue under high vacuum yielded the crude title compound (3.20 g, 93%) that was used further without purification. LC-MS: $t_R$=0.90 min; ES+: 341.18.

{2-[3-(tert-Butyl-dimethyl-silanyloxymethyl)-4-chloro-phenyl]-ethyl}-methyl-carbamic acid tert-butyl ester $K_2CO_3$ (728 mg, 5.27 mmol) and methyl chloroformate (0.405 mL, 5.27 mmol) were added to a sol. of 2-[3-(tert-butyl-dimethyl-silanyloxymethyl)-4-chloro-phenyl]-ethylamine (1.05 g mg, 3.51 mmol) in $CH_2Cl_2$ (36 mL). The mixture was stirred at rt for 1 h and methyl chloroformate (0.304 mL, 3.95 mmol) was added again. The mixture was stirred at rt for 1 h and methyl chloroformate (0.304 mL, 3.95 mmol) was added again. The mixture was stirred at rt for 1 h, and $CH_2Cl_2$ (30 mL) was added. The resulting mixture was washed with aq. sat. $NH_4Cl$ (2×), aq. 10% $K_2CO_3$ (1×) and brine (1×). The org. layer was dried over $MgSO_4$, filtered, and the solvents were removed under reduced pressure to yield the crude {2-[3-(tert-butyl-dimethyl-silanyloxymethyl)-4-chloro-phenyl]-ethyl}-carbamic acid methyl ester. This crude product was dissolved in THF (36 mL). The sol. was cooled to 0° C., and $LiAlH_4$ (400 mg, 10.5 mmol) was carefully added in portions. The mixture was allowed to warm up to rt, and was stirred at rt overnight. The mixture was poured onto aq. sat. potassium sodium tartrate (50 mL), and the mixture was stirred at rt for 2 h. The mixture was extracted with $Et_2O$ (3×). The combined org. extracts were dried over $MgSO_4$, filtered, and the solvents were removed under reduced pressure to yield the crude {2-[3-(tert-butyl-dimethyl-silanyloxymethyl)-4-chloro-phenyl]-ethyl}-methyl-amine. This crude product was dissolved in $CH_2Cl_2$ (36 mL). DIPEA (1.80 mL, 10.5 mmol) was added, followed by $Boc_2O$ (2.30 g, 10.5 mmol). The mixture was stirred at rt for 1 h, and $CH_2Cl_2$ (50 mL) was added. The mixture was washed with aq. 1M HCl, brine, aq. sat. $NaHCO_3$, and brine. The org. layer was dried over $MgSO_4$, filtered, and the solvents were removed under reduced pressure. Purification of the crude by FC (EtOAc/heptane 4:1) yielded the title compound (1.00 g, 91%). LC-MS: $t_R$=0.84 min; ES+: 355.23.

[2-(4-Chloro-3-hydroxymethyl-phenyl)-ethyl]-methyl-carbamic acid tert-butyl ester TBAF (1M in THF, 2.90 mL, 2.90 mmol) was added to a sol. of {2-[3-(tert-butyl-dimethyl-silanyloxymethyl)-4-chloro-phenyl]-ethyl}-methyl-carbamic acid tert-butyl ester (600 mg, 1.45 mmol) in THF (14.2 mL) at 0° C. The mixture was stirred for 1 h while warming up to rt. EtOAc was added, and the mixture was washed with aq. sat. $NH_4Cl$ and brine. The org. layer was dried over $MgSO_4$, filtered, and the solvents were removed under reduced pressure. Purification of the crude by FC ($CH_2Cl_2$/MeOH 19:1) yielded the title compound (435 mg, quantitative yield). LC-MS: $t_R$=0.93 min.

[2-(4-Chloro-3-formyl-phenyl)-ethyl]-methyl-carbamic acid tert-butyl ester

NMO (607 mg, 4.35 mmol) was added to a sol. of [2-(4-chloro-3-hydroxymethyl-phenyl)-ethyl]-methyl-carbamic acid tert-butyl ester (435 mg, 1.45 mmol) in $CH_2Cl_2$ (30 mL). The mixture was stirred for 30 min, and tetrapropylammonium perrhutenate (51.0 mg, 0.145 mmol) was added. The mixture was stirred for 1 h, and was filtered over Celite. The filtrate was evaporated under reduced pressure. Purification of the crude by FC ($CH_2Cl_2$/MeOH 19:1) yielded the title compound (330 mg, 76%). LC-MS: $t_R$=1.00 min.

[2-(4-Chloro-3-cyclopropylaminomethyl-phenyl)-ethyl]-methyl-carbamic acid tert-butyl ester A mixture of [2-(4-chloro-3-formyl-phenyl)-ethyl]-methyl-carbamic acid tert-butyl ester (325 mg, 1.09 mmol), $Et_3N$ (0.228 mL, 1.64 mmol) and cyclopropylamine (0.115 mL, 1.64 mmol) in MeOH (3.66 mL) was heated to reflux for 4 h. The mixture was allowed to cool to rt, and $NaBH_4$ (103 mg, 2.73 mmol) was added. The mixture was stirred for 1 h at rt, and aq. sat. $NaHCO_3$ was added. The mixture was extracted with EtOAc several times. The combined org. extracts were dried over $MgSO_4$, filtered, and the solvents were removed under reduced pressure. Purification of the crude by FC yielded the title compound (186 mg, 50%). LC-MS: $t_R$=0.79 min; ES+: 339.39.

[3-(tert-Butyl-dimethyl-silanyloxymethyl)-4-chloro-benzyl]-methyl-carbamic acid tert-butyl ester $K_2CO_3$ (363 mg, 2.63 mmol) and methyl chloroformate (0.202 mL, 2.63 mmol) were added to a sol. of 3-(tert-butyl-dimethyl-silanyloxymethyl)-4-chloro-benzylamine (500 mg, 1.76 mmol) in $CH_2Cl_2$ (18 mL). The mixture was stirred at rt for 1 h and methyl chloroformate (0.151 mL, 1.97 mmol) was added again. The mixture was stirred at rt for 1 h, and $CH_2Cl_2$ (30 mL) was added. The resulting mixture was washed with aq. sat. $NH_4Cl$ (2×), aq. 10% $K_2CO_3$ (1×) and brine (1×). The org. layer was dried over $MgSO_4$, filtered, and the solvents were removed under reduced pressure to yield the crude [3-(tert-butyl-dimethyl-silanyloxymethyl)-4-chloro-benzyl]-carbamic acid methyl ester. This crude product was dissolved in THF (18 mL). The sol. was cooled to 0° C., and $LiAlH_4$ (200 mg, 5.27 mmol) was carefully added in portions. The mixture was allowed to warm up to rt, and was stirred at rt overnight. The mixture was poured onto aq. sat. potassium sodium tartrate (50 mL), and the mixture was stirred at rt for 2 h. The mixture was extracted with EtOAc (3×). The combined org. extracts were dried over $MgSO_4$, filtered, and the solvents were removed under reduced pressure to yield the crude [3-(tert-butyl-dimethyl-silanyloxymethyl)-4-chloro-benzyl]-methyl-amine. This crude product was dissolved in $CH_2Cl_2$ (18 mL). DIPEA (0.900 mL, 5.26 mmol) was added, followed by $Boc_2O$ (1.15 g, 5.27 mmol). The mixture was stirred at rt overnight, and $CH_2Cl_2$ (50 mL) was added. The mixture was washed with aq. 1M HCl, brine, aq. sat. $NaHCO_3$, and brine. The org. layer was dried over $MgSO_4$, filtered, and the solvents were removed under reduced pressure. Purification of the crude by FC (EtOAc/heptane 50:50) yielded a mixture (0.900 g) of the title compound, $Boc_2O$, and [3-(tert-butyl-dimethyl-silanyloxymethyl)-benzyl]-methyl-carbamic acid tert-butyl ester. This crude mixture, wherein the title compound accounted for 439 mg (83%) was used further without purification. LC-MS: $t_R$=1.10 min; ES+: 344.13.

(4-Chloro-3-hydroxymethyl-benzyl)-methyl-carbamic acid tert-butyl ester

TBAF (1M in THF, 2.25 mL, 2.25 mmol) was added to a sol. of [3-(tert-butyl-dimethyl-silanyloxymethyl)-4-chloro-benzyl]-methyl-carbamic acid tert-butyl ester (450 mg, 1.13 mmol) in THF (11 mL) at 0° C. The mixture was stirred for 1 h while warming up to rt. EtOAc (50 mL) was added, and the resulting mixture was washed with aq. sat. $NH_4Cl$ (2×) and brine (1×). The org. layer was dried over $MgSO_4$, filtered, and the solvents were removed under reduced pressure. Purification of the crude by FC (EtOAc/heptane 40:60) yielded the title compound (110 mg, 34%). LC-MS: $t_R$=0.91 min; ES+: 271.10.

(4-Chloro-3-formyl-benzyl)-methyl-carbamic acid tert-butyl ester

MnO$_2$ (372 mg, 3.85 mmol) was added to a sol. of (4-chloro-3-hydroxymethyl-benzyl)-methyl-carbamic acid tert-butyl ester (110 mg, 0.385 mmol) in CH$_3$CN (7.70 mL). The mixture was stirred at rt for 4.5 h, and MnO$_2$ (186 mg, 1.93 mmol) was added again. The mixture was stirred for 1 h, and the mixture was filtered over Celite. The precipitate was washed with CH$_3$CN and CH$_2$Cl$_2$. The filtrate was evaporated under reduced pressure. Drying the residue under high vacuum yielded the crude title compound (95 mg, 87%) that was used further without purification. LC-MS: $t_R$=0.99 min.

(4-Chloro-3-cyclopropylaminomethyl-benzyl)-methyl-carbamic acid tert-butyl ester A mixture of (4-chloro-3-formyl-benzyl)-methyl-carbamic acid tert-butyl ester (95 mg, 0.335 mmol) and cyclopropylamine (0.036 mL, 0.50 mmol) in MeOH (3.30 mL) was heated to reflux for 4 h. The mixture was allowed to cool to rt, and NaBH$_4$ (19 mg, 0.50 mmol) was added in portions. The mixture was stirred for 1 h, and the solvents were removed under reduced pressure. The resulting oil was diluted with EtOAc (20 mL), and this mixture was washed with aq. sat. NaHCO$_3$ and brine. The org. layer was dried over MgSO$_4$, filtered, and the solvents were removed under reduced pressure. Purification of the residue by FC (CH$_2$Cl$_2$/MeOH 90:10) yielded the title compound (81 mg, 75%). LC-MS: $t_R$=0.73 min; ES+: 366.20.

N-{2-[3-(tert-Butyl-dimethyl-silanyloxymethyl)-4-chloro-phenyl]-ethyl}-3,3,3-trifluoro-propionamide TBTU (2.09 g, 6.50 mmol) was added to a sol. of 2-[3-(tert-butyl-dimethyl-silanyloxymethyl)-4-chloro-phenyl]-ethylamine (1.30 g, 4.33 mmol), 3,3,3-trifluoropropionic acid (0.574 mL, 6.50 mmol) and DIPEA (2.97 mL, 17.3 mmol) in CH$_2$Cl$_2$ (43 mL). The mixture was stirred for 1 h, and CH$_2$Cl$_2$ was added. The mixture was washed with aq. sat. NH$_4$Cl, aq. 10% Na$_2$CO$_3$ and brine. The org. layer was dried over MgSO$_4$, filtered, and the solvents were removed under reduced pressure. Purification of the crude by FC (EtOAc/heptane 60:40) yielded the title compound (500 mg, 28%). LC-MS: $t_R$=1.12 min; ES+: 410.14.

N-[2-(4-Chloro-3-hydroxymethyl-phenyl)-ethyl]-3,3,3-trifluoro-propionamide

TBAF (1M in THF, 2.46 mL, 2.46 mmol) was added to a sol. of N-{2-[3-(tert-butyl-dimethyl-silanyloxymethyl)-4-chloro-phenyl]-ethyl}-3,3,3-trifluoro-propionamide (500 mg, 1.22 mmol) in THF (15.8 mL) at 0° C. The mixture was stirred for 1 h at 0° C., and aq. sat. NH$_4$Cl was added. The mixture was extracted with EtOAc (3×). The combined org. extracts were washed with water (4×), dried over MgSO$_4$, filtered, and the solvents were removed under reduced pressure. Purification of the residue by FC (CH$_2$Cl$_2$/MeOH 19:1) yielded the title compound (230 mg, 64%). LC-MS: $t_R$=0.79 min.

N-[2-(4-Chloro-3-formyl-phenyl)-ethyl]-3,3,3-trifluoro-propionamide

NMO (318 mg, 2.28 mmol) was added to a sol. of N-[2-(4-chloro-3-hydroxymethyl-phenyl)-ethyl]-3,3,3-trifluoro-propionamide (225 mg, 0.761 mmol) in CH$_2$Cl$_2$ (16 mL). The mixture was stirred for 30 min, and tetrapropylammonium perruthenate (26.7 mg, 0.076 mmol) was added. The mixture was stirred for 1 h at rt, and was filtered over Celite. The filtrate was evaporated under reduced pressure. Purification of the crude by FC (CH$_2$Cl$_2$/MeOH 19:1) yielded the title compound (180 mg, 81%). LC-MS: $t_R$=0.88 min; ES+: 335.28.

N-[2-(4-Chloro-3-cyclopropylaminomethyl-phenyl)-ethyl]-3,3,3-trifluoro-propionamide A mixture of N-[2-(4-chloro-3-formyl-phenyl)-ethyl]-3,3,3-trifluoro-propionamide (175 mg, 0.596 mmol), Et$_3$N (0.125 mL, 0.896 mmol) and cyclopropylamine (0.063 mL, 0.90 mmol) in MeOH (2.00 mL) was heated to reflux for 4 h. The mixture was allowed to cool to rt, and NaBH$_4$ (56.4 mg, 1.49 mmol) was added in portions. The mixture was stirred for 1 h, and aq. sat. NaHCO$_3$ was added. The mixture was extracted with EtOAc several times, and the combined org. extracts were washed with brine. The org. layer was dried over MgSO$_4$, filtered, and the solvents were removed under reduced pressure. Purification of the residue by FC (CH$_2$Cl$_2$/MeOH 95:5) yielded the title compound (130 mg, 65%). LC-MS: $t_R$=0.65 min; ES+: 335.12.

{2-[3-(tert-Butyl-dimethyl-silanyloxymethyl)-4-chloro-phenyl]-ethyl}-ethyl-amine A mixture of 2-[3-(tert-butyl-dimethyl-silanyloxymethyl)-4-chloro-phenyl]-ethylamine (1.05 g, 3.50 mmol) and acetaldehyde (1.19 mL, 21.0 mmol) in MeOH (35 mL) was heated to reflux for 4 h. The mixture was allowed to cool to rt and NaBH$_4$ (198 mg, 5.25 mmol) was added in portions. The mixture was stirred at rt for 1 h, and the solvents were removed under reduced pressure. The resulting oil was diluted with EtOAc, and the mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 19:1→9:1) yielded the title compound (320 mg, 28%). LC-MS: $t_R$=0.90 min; ES+: 369.22.

{2-[3-(tert-Butyl-dimethyl-silanyloxymethyl)-4-chloro-phenyl]-ethyl}-ethyl-carbamic acid tert-butyl ester A mixture of {2-[3-(tert-butyl-dimethyl-silanyloxymethyl)-4-chloro-phenyl]-ethyl}-ethyl-amine (320 mg, 0.976 mmol), DIPEA (0.501 mL, 2.93 mmol) and Boc$_2$O (320 mg, 1.47 mmol) in CH$_2$Cl$_2$ (10 mL) was stirred at rt for 2 h. CH$_2$Cl$_2$ (30 mL) was added, and the mixture was washed with aq. HCl 1M, aq. sat. NaHCO$_3$ and brine. The org. layer was dried over MgSO$_4$, filtered, and the solvents were removed under reduced pressure. Purification of the crude by FC (EtOAc/heptane 20:80) yielded the title compound (298 mg, 71%). LC-MS: $t_R$=1.25 min; ES+: 428.19.

[2-(4-Chloro-3-hydroxymethyl-phenyl)-ethyl]-ethyl-carbamic acid tert-butyl ester TBAF (1M in THF, 1.39 mL, 1.39 mmol) was added to a sol. of {2-[3-(tert-butyl-dimethyl-silanyloxymethyl)-4-chloro-phenyl]-ethyl}-ethyl-carbamic acid tert-butyl ester (298 mg, 0.696 mmol) in THF (6.82 mL) at 0° C. The mixture was stirred for 1 h while warming up to rt. EtOAc was added, and the mixture was washed with aq. sat. NH$_4$Cl and brine. The org. layer was dried over MgSO$_4$, filtered, and the solvents were removed under reduced pressure. Purification of the crude by FC (CH$_2$Cl$_2$/MeOH 19:1) yielded the title compound (110 mg, 50%). LC-MS: $t_R$=0.97 min; ES+: 314.11.

[2-(4-Chloro-3-formyl-phenyl)-ethyl]-ethyl-carbamic acid tert-butyl ester

NMO (133 mg, 0.956 mmol) was added to a sol. of [2-(4-chloro-3-hydroxymethyl-phenyl)-ethyl]-ethyl-carbamic acid tert-butyl ester (110 mg, 0.319 mmol) in CH$_2$Cl$_2$ (7.0 mL). The mixture was stirred for 30 min, and tetrapropylammonium perruthenate (11.2 mg, 0.032 mmol) was added. The mixture was stirred for 1 h at rt, and was filtered over Celite. The filtrate was evaporated under reduced pressure. Purification of the crude by FC (CH$_2$Cl$_2$/MeOH 49:1) yielded the title compound (80 mg, 80%). LC-MS: $t_R$=1.07 min.

[2-(4-Chloro-3-cyclopropylaminomethyl-phenyl)-ethyl]-ethyl-carbamic acid tert-butyl ester A mixture of [2-(4-chloro-3-formyl-phenyl)-ethyl]-ethyl-carbamic acid tert-butyl ester (80.1 mg, 0.257 mmol), Et$_3$N (0.054 mL, 0.386 mmol) and cyclopropylamine (0.027 mL, 0.386 mmol) in MeOH (0.86 mL) was heated to reflux for 4 h. The mixture was allowed to cool to rt, and NaBH$_4$ (24.2 mg, 0.642 mmol) was added in portions. The mixture was stirred for 1 h, and aq. sat. NaHCO$_3$ was added. The mixture was extracted with EtOAc several times, and the combined org. extracts were washed with brine. The org. layer was dried over MgSO$_4$, filtered, and the solvents were removed under reduced pressure. Purification of the residue by FC (CH$_2$Cl$_2$/MeOH 95:5) yielded the title compound (40 mg, 44%). LC-MS: $t_R$=0.81 min; ES+: 353.22.

N-{2-[3-(tert-Butyl-dimethyl-silanyloxymethyl)-4-chloro-phenyl]-ethyl}-acetamide AcCl (0.063 mL, 0.88 mmol) was added to a sol. of 2-[3-(tert-butyl-dimethyl-silanyloxymethyl)-4-chloro-phenyl]-ethylamine (252 mg, 0.840 mmol) and DIPEA (0.575 mL, 3.36 mmol) in CH$_2$Cl$_2$ (8.4 mL). The mixture was stirred at rt for 30 min, and aq. sat. NH$_4$Cl was added. The layers were separated, and the org. layer was washed with aq. 1M NaOH, dried over MgSO$_4$, filtered, and the solvents were removed under reduced pressure. Purification of the crude by FC (CH$_2$Cl$_2$/MeOH 19:1) yielded the title compound (190 mg, 66%). LC-MS: $t_R$=1.09 min; ES+: 342.19.

N-[2-(4-Chloro-3-hydroxymethyl-phenyl)-ethyl]-acetamide

TBAF (1M in THF, 1.12 mL, 1.12 mmol) was added to a sol. of N-{2-[3-(tert-butyl-dimethyl-silanyloxymethyl)-4-chloro-phenyl]-ethyl}-acetamide (190 mg, 0.555 mmol) in THF (7.10 mL) at 0° C. The mixture was stirred for 1 h while warming up to rt. Aq. sat. NH$_4$Cl was added, and the mixture was extracted with EtOAc (3×). The org. layer was dried over MgSO$_4$, filtered, and the solvents were removed under reduced pressure. Purification of the crude by FC (CH$_2$Cl$_2$/MeOH 19:1) yielded the title compound (100 mg, 79%). LC-MS: $t_R$=0.67 min; ES+: 284.11.

N-[2-(4-Chloro-3-formyl-phenyl)-ethyl]-acetamide

NMO (184 mg, 1.32 mmol) was added to a sol. of N-[2-(4-chloro-3-hydroxymethyl-phenyl)-ethyl]-acetamide (100 mg, 0.439 mmol) in CH$_2$Cl$_2$ (9.22 mL). The mixture was stirred for 30 min, and tetrapropylammonium perruthenate (15.5 mg, 0.044 mmol) was added. The mixture was stirred for 1 h at rt, and was filtered over Celite. The filtrate was evaporated under reduced pressure. Purification of the crude by FC (CH$_2$Cl$_2$/MeOH 49:1) yielded the title compound (50 mg, 50%). LC-MS: $t_R$=0.75 min; ES+: 267.10.

N-[2-(4-Chloro-3-cyclopropylaminomethyl-phenyl)-ethyl]-acetamide

A mixture of N-[2-(4-chloro-3-formyl-phenyl)-ethyl]-acetamide (50.1 mg, 0.222 mmol), Et$_3$N (0.046 mL, 0.332 mmol) and cyclopropylamine (0.023 mL, 0.332 mmol) in MeOH (0.50 mL) was heated to reflux for 4 h. The mixture was allowed to cool to rt, and NaBH$_4$ (21.0 mg, 0.554 mmol) was added in portions. The mixture was stirred for 1 h, and aq. sat. NaHCO$_3$ was added. The mixture was extracted with EtOAc several times, and the combined org. extracts were washed with brine. The org. layer was dried over MgSO$_4$, filtered, and the solvents were removed under reduced pressure. Purification of the residue by FC (CH$_2$Cl$_2$/MeOH 95:5) yielded the title compound (35 mg, 59%). LC-MS: $t_R$=0.59 min; ES+: 267.17.

[3-(tert-Butyl-dimethyl-silanyloxymethyl)-4-chloro-benzyl]-(2-fluoro-ethyl)-carbamic acid tert-butyl ester A mixture of 3-(tert-butyl-dimethyl-silanyloxymethyl)-4-chloro-benzaldehyde (1.50 g, 5.27 mmol), DIPEA (1.80 mL, 10.5 mmol) and 2-fluoroethylamine hydrochloride (873 mg, 7.90 mmol) in MeOH (53 mL) was heated to reflux for 4 h. The reaction was allowed to cool to rt, and NaBH$_4$ (300 mg, 7.91 mmol) was added in portions. The mixture was stirred for 1 h, and the solvents were removed under reduced pressure. EtOAc (100 mL) was added, and the mixture was washed with aq. sat. NaHCO$_3$ and brine. The org. layer was dried over MgSO$_4$, filtered, and the solvents were removed under reduced pressure to yield the crude [3-(tert-butyl-dimethyl-silanyloxymethyl)-4-chloro-benzyl]-(2-fluoro-ethyl)-amine. This crude product was dissolved in CH$_2$Cl$_2$ (70 mL). DIPEA (2.70 mL, 15.8 mmol) was added, followed by Boc$_2$O (1.70 g, 7.91 mmol). The mixture was stirred at rt for 1 h. The mixture was diluted with CH$_2$Cl$_2$ (50 mL), and was washed with aq. 1M HCl, aq. sat. NaHCO$_3$ and brine. The org. layer was dried over MgSO$_4$, filtered, and the solvents were removed under reduced pressure. Purification of the crude by FC (EtOAc/heptane 10:90) yielded the title compound (1.92 g, 85%). LC-MS: $t_R$=1.22 min; ES+: 417.17.

(4-Chloro-3-hydroxymethyl-benzyl)-(2-fluoro-ethyl)-carbamic acid tert-butyl ester TBAF (1M in THF, 8.84 mL, 8.84 mmol) was added to a sol. of [3-(tert-butyl-dimethyl-silanyloxymethyl)-4-chloro-benzyl]-(2-fluoro-ethyl)-carbamic acid tert-butyl ester (1.91 g, 4.42 mmol) in THF (44.2 mL) at 0° C. The mixture was stirred for 1 h while warming up to rt. EtOAc (100 mL) was added, and the resulting mixture was washed with aq. sat. NH$_4$Cl (2×) and brine (1×). The org. layer was dried over MgSO$_4$, filtered, and the solvents were removed under reduced pressure. Purification of the crude by FC (EtOAc/heptane 30:70) yielded the title compound (901 mg, 64%). LC-MS: t$_R$=0.64 min; ES+: 318.07.

(4-Chloro-3-formyl-benzyl)-(2-fluoro-ethyl)-carbamic acid tert-butyl ester

MnO$_2$ (1.22 g, 12.6 mmol) was added to a sol. of (4-chloro-3-hydroxymethyl-benzyl)-(2-fluoro-ethyl)-carbamic acid tert-butyl ester (801 mg, 2.52 mmol) in CH$_3$CN (50 mL). The mixture was stirred at rt for 4.5 h, and MnO$_2$ (1.22 g, 12.6 mmol) was added again. The mixture was stirred for 1 h, and was filtered over Celite. The precipitate was washed with CH$_3$CN and CH$_2$Cl$_2$. The filtrate was evaporated under reduced pressure. Drying the residue under high vacuum yielded the crude title compound (800 mg, quantitative yield) that was used further without purification. LC-MS: t$_R$=1.01 min.

(4-Chloro-3-cyclopropylaminomethyl-benzyl)-(2-fluoro-ethyl)-carbamic acid tert-butyl ester A mixture of (4-chloro-3-formyl-benzyl)-(2-fluoro-ethyl)-carbamic acid tert-butyl ester (850 mg, 2.69 mmol) and cyclopropylamine (0.290 mL, 4.05 mmol) in MeOH (27 mL) was heated to reflux for 4 h. The mixture was allowed to cool to rt, and NaBH$_4$ (153 mg, 4.40 mmol) was added in portions. The mixture was stirred for 1 h. The solvents were removed under reduced pressure, and EtOAc was added. The resulting mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 95:5) yielded the title compound (845 mg, 88%). LC-MS: t$_R$=0.76 min; ES+: 357.19.

[3-(tert-Butyl-dimethyl-silanyloxymethyl)-4-chloro-benzyl]-ethyl-carbamic acid tert-butyl ester Acetaldehyde (2.4 mL, 42 mmol) was added to a sol of 3-(tert-butyl-dimethyl-silanyloxymethyl)-4-chloro-benzylamine (2.00 g, 7.00 mmol) in MeOH (70 mL). The mixture was heated to reflux for 4 h, and was allowed to cool to rt. NaBH$_4$ (397 mg, 10.5 mmol) was added in portions over 1 h. The solvents were removed under reduced pressure. The residue was diluted with EtOAc (100 mL), and the resulting mixture was washed with aq. sat. NaHCO$_3$ and brine. The org. layer was dried over MgSO$_4$, filtered, and the solvents were removed under reduced pressure to yield the crude [3-(tert-butyl-dimethyl-silanyloxymethyl)-4-chloro-benzyl]-ethyl-amine (3.07 g). This crude material was dissolved in CH$_2$Cl$_2$ (70 mL). DIPEA (3.60 mL, 21.0 mmol) was added, followed by Boc$_2$O (2.29 g, 10.5 mmol). The mixture was stirred at rt for 2 h. The mixture was diluted with CH$_2$Cl$_2$ (30 mL), and was washed with aq. 1M HCl, aq. sat. NaHCO$_3$ and brine. The org. layer was dried over MgSO$_4$, filtered, and the solvents were removed under reduced pressure. Purification of the crude by FC (EtOAc/heptane 5:95) yielded the title compound (850 mg, 29%). LC-MS: t$_R$=1.23 min; ES+: 414.23.

(4-Chloro-3-hydroxymethyl-benzyl)-ethyl-carbamic acid tert-butyl ester

TBAF (1M in THF, 3.03 mL, 3.03 mmol) was added dropwise to a sol. of [3-(tert-butyl-dimethyl-silanyloxymethyl)-4-chloro-benzyl]-ethyl-carbamic acid tert-butyl ester (628 mg, 1.52 mmol) in THF (14.9 mL) at 0° C. The mixture was stirred for 1 h while warming up to rt. EtOAc was added, and the mixture was washed with aq. sat. NH$_4$Cl and brine. The org. layer was dried over MgSO$_4$, filtered, and the solvents were removed under reduced pressure. Purification of the crude by FC (MeOH/CH$_2$Cl$_2$ 19:1) yielded the title compound (300 mg, 66%). LC-MS: t$_R$=0.98 min; ES+: 300.28.

(4-Chloro-3-formyl-benzyl)-ethyl-carbamic acid tert-butyl ester

MnO$_2$ (475 mg, 4.92 mmol) was added to a sol. of (4-chloro-3-hydroxymethyl-benzyl)-ethyl-carbamic acid tert-butyl ester (295 mg, 0.984 mmol) in CH$_3$CN (20 mL). The mixture was stirred at rt for 5 h and MnO$_2$ (475 mg, 0.984 mmol) was added again. The mixture was stirred for 1 h, and the mixture was filtered over Celite, and washed with CH$_3$CN and CH$_2$Cl$_2$. Evaporation of the solvents under reduced pressure yielded the crude title compound (240 mg, 82%) that was used further without purification. LC-MS: t$_R$=1.02 min.

(4-Chloro-3-cyclopropylaminomethyl-benzyl)-ethyl-carbamic acid tert-butyl ester A mixture of (4-chloro-3-formyl-benzyl)-ethyl-carbamic acid tert-butyl ester (240 mg, 0.806 mmol), cyclopropylamine (0.085 mL, 1.2 mmol) and Et$_3$N (0.169 mL, 1.21 mmol) in MeOH (2.7 mL) was heated to reflux for 4 h. The mixture was allowed to cool to rt, and NaBH$_4$ (76.2 mg, 2.01 mmol) was added. The mixture was stirred for 1 h at rt, and aq. sat. NaHCO$_3$ was added. The mixture was extracted several times with EtOAc. The combined org. extracts were dried over MgSO$_4$, filtered, and the solvents were removed under reduced pressure. Purification of the crude by FC (MeOH/CH$_2$Cl$_2$ 1:49) yielded the title compound (125 mg, 46%). LC-MS: t$_R$=0.78 min; ES+: 380.20.

[3-(tert-Butyl-dimethyl-silanyloxymethyl)-4-chloro-benzyl]-cyclopropyl-carbamic acid tert-butyl ester A mixture of 3-(tert-butyl-dimethyl-silanyloxymethyl)-4-chloro-benzaldehyde (1.73 g, 6.06 mmol) and cyclopropylamine (0.64 mL, 9.1 mmol) in MeOH (60 mL) was heated to reflux for 4 h. The mixture was allowed to cool to rt, and NaBH$_4$ (344 mg, 9.09 mmol) was added in portions. The mixture was stirred for 1 h, and water (20 mL) was added. The solvents were partially removed under reduced pressure. The resulting aq. suspension was diluted with water (50 mL), and extracted with EtOAc. The org. extracts were washed with aq. sat. NaHCO$_3$, and brine. The org. layer was dried over MgSO$_4$, filtered, and the solvents were removed under reduced pressure to yield the crude [3-(tert-butyl-dimethyl-silanyloxymethyl)-4-chloro-benzyl]-cyclopropyl-amine (1.54 g). This crude material was dissolved in CH$_2$Cl$_2$ (60 mL). DIPEA (3.1 mL, 18 mmol) was added, followed by Boc$_2$O (1.98 g, 9.09 mmol). The mixture was stirred at rt for 2 h. CH$_2$Cl$_2$ (40 mL) was added, and the mixture was washed with aq. 1M HCl, aq. sat. NaHCO$_3$ and brine. The org. layer was dried over MgSO$_4$, filtered, and the solvents were removed under reduced pressure. Purification of the crude by FC (heptane→EtOAc/heptane 5:95) yielded the title compound (1.54 g, 78%). LC-MS: t$_R$=1.26 min; ES+: 426.14.

(4-Chloro-3-hydroxymethyl-benzyl)-cyclopropyl-carbamic acid tert-butyl ester Aq. 1M NaOH (16 mL) was added to a sol. of [3-(tert-butyl-dimethyl-silanyloxymethyl)-4-chloro-benzyl]-cyclopropyl-carbamic acid tert-butyl ester (700 mg, 1.64 mmol) in MeOH (32 mL). The mixture was heated to reflux for 2 h, and was allowed to cool to rt. The solvents were partially removed under reduced pressure, and the resulting aq. layer was diluted with water (100 mL). The mixture was extracted with $Et_2O$ (3×). The combined org. layers were dried over $MgSO_4$, filtered, and the solvents were removed under reduced pressure. Purification of the crude by FC (EtOAc/heptane 40:60) yielded the title compound (550 mg, quantitative yield). LC-MS: $t_R$=0.98 min; ES+: 312.04.

(4-Chloro-3-formyl-benzyl)-cyclopropyl-carbamic acid tert-butyl ester $MnO_2$ (815 mg, 8.44 mmol) was added to a sol. of (4-chloro-3-hydroxymethyl-benzyl)-cyclopropyl-carbamic acid tert-butyl ester (526 mg, 1.69 mmol) in $CH_3CN$ (34 mL). The mixture was stirred at rt for 3 h, and was filtered over Celite, and washed with $CH_3CN$ and $CH_2Cl_2$. Evaporation of the solvents under reduced pressure yielded the crude title compound (563 mg, quantitative yield) that was used further without purification. LC-MS: $t_R$=1.05 min; ES+: 310.04.

(4-Chloro-3-cyclopropylaminomethyl-benzyl)-cyclopropyl-carbamic acid tert-butyl ester A mixture of (4-chloro-3-formyl-benzyl)-cyclopropyl-carbamic acid tert-butyl ester (563 mg, 1.82 mmol) and cyclopropylamine (0.195 mL, 2.73 mmol) in MeOH (18 mL) was heated to reflux for 4 h. The mixture was allowed to cool to rt, and $NaBH_4$ (103 mg, 2.73 mmol) was added in portions. The mixture was stirred for 1 h, and the solvents were removed under reduced pressure. The resulting oil was diluted with EtOAc (100 mL), and the resulting mixture was washed with aq. sat. $NaHCO_3$ and brine. The org. layer was dried over $MgSO_4$, filtered, and the solvents were removed under reduced pressure. Purification of the crude by FC ($CH_2Cl_2$/MeOH 95:5) yielded the title compound (343 mg, 54%). LC-MS: $t_R$=0.78 min; ES+: 351.39.

tert-Butyl-(2-chloro-5-vinyl-benzyloxy)-dimethyl-silane $Pd(PPh_3)_4$ (173 mg, 0.149 mmol) was added to a sol. of (5-bromo-2-chloro-benzyloxy)-tert-butyl-dimethyl-silane (1.00 g, 2.98 mmol) in dimethoxyethane (30 mL). The mixture was stirred at rt for 20 min, and $K_2CO_3$ (411 mg, 2.98 mmol), water (10 mL) and 4,4,5,5-tetramethyl-2-vinyl-1,3,2-dioxaborolane (0.53 mL, 2.98 mmol) were added. The mixture was heated rapidly to reflux, and stirred under reflux for 2 h. The mixture was allowed to cool to rt, and was diluted with $Et_2O$ (100 mL). The mixture was washed with water, and the aq. layer was extracted back with $Et_2O$ (3×). The combined org. extracts were dried over $MgSO_4$, filtered, and the solvents were removed under reduced pressure. Purification of the crude by FC (EtOAc/heptane 5:95) yielded the title compound (822 mg, 98%). LC-MS: $t_R$=1.22 min.

2-[3-(tert-Butyl-dimethyl-silanyloxymethyl)-4-chloro-phenyl]-ethanol

9-BBN (0.5M in THF, 34.0 mL, 17.0 mmol) was added dropwise over 30 min to a sol. of tert-butyl-(2-chloro-5-vinyl-benzyloxy)-dimethyl-silane (800 mg, 2.83 mmol) in THF (28 mL) at 0° C. The mixture was stirred for 30 min at 0°, and for 4 h at rt. The mixture was cooled again to 0° C., and aq. 1M NaOH (39.0 mL) and $H_2O_2$ (33%, 9.8 mL, 113 mmol) were added dropwise. The mixture was stirred for 2 h while warming up to rt, and was cooled to 0° C. Aq. sat. $Na_2S_2O_3$ (100 mL) was carefully added, and this mixture was allowed to gently warm up to rt overnight. The solvents were partially removed under reduced pressure, and the aq. residue was extracted with EtOAc (3×). The combined org. extracts were washed with brine. The org. layer was dried over $MgSO_4$, filtered, and the solvents were removed under reduced pressure. Purification of the crude by FC (EtOAc/heptane 40:60) yielded the title compound (677 mg, 80%). LC-MS: $t_R$=1.10 min; ES+: 301.08.

Methanesulfonic acid 2-[3-(tert-butyl-dimethyl-silanyloxymethyl)-4-chloro-phenyl]-ethyl ester To a sol. of 2-[3-(tert-butyl-dimethyl-silanyloxymethyl)-4-chloro-phenyl]-ethanol (2.00 g, 6.65 mmol) in $CH_2Cl_2$ (66 mL) at 0° C. were added dropwise $Et_3N$ (1.02 mL, 7.31 mmol) and methanesulfonyl chloride (0.57 mL, 7.31 mmol). The reaction was stirred at 0° C. for 1 h, and was diluted with $CH_2Cl_2$ (40 mL). The resulting mixture was washed with aq. sat. $NH_4Cl$ (2×). The org. layer was dried over $MgSO_4$, filtered, and the solvents were removed under reduced pressure to yield the crude title compound (2.55 g, quantitative yield) that was used further without purification. LC-MS: $t_R$=1.13 min; ES+: 379.29.

{2-[3-(tert-Butyl-dimethyl-silanyloxymethyl)-4-chloro-phenyl]-ethyl}-cyclopropyl-amine Cyclopropylamine (1.14 mL, 16.3 mmol) was added to a sol. of methanesulfonic acid 2-[3-(tert-butyl-dimethyl-silanyloxymethyl)-4-chloro-phenyl]-ethyl ester (1.76 g, 4.65 mmol) in EtOH (46 mL). The mixture was heated to reflux for 2 h, and cyclopropylamine (0.57 mL, 8.2 mmol) was added again. The mixture was heated to reflux overnight, and was allowed to cool to rt. The solvents were removed under reduced pressure, and the residue was purified by FC (EtOAc/heptane 50:50→7M $NH_3$/MeOH) to yield the title compound (865 mg, 68%). LC-MS: $t_R$=0.92 min; ES+: 340.39.

{2-[3-(tert-Butyl-dimethyl-silanyloxymethyl)-4-chloro-phenyl]-ethyl}-cyclopropyl-carbamic acid tert-butyl ester DIPEA (2.61 mL, 5.60 mmol) and $Boc_2O$ (1.22 g, 5.60 mmol) were added to a sol. of {2-[3-(tert-butyl-dimethyl-silanyloxymethyl)-4-chloro-phenyl]-ethyl}-cyclopropyl-amine (1.73 g, 5.09 mmol) in $CH_2Cl_2$ (50 mL). The mixture was stirred at rt for 4 h. The mixture was diluted with $CH_2Cl_2$ (50 mL), washed with aq. sat. $NaHCO_3$, aq. sat. $NH_4Cl$ and brine. The org. layer was dried over $MgSO_4$, filtered, the solvents were removed under reduced pressure. Purification of the crude by FC (EtOAc/heptane 10:90) yielded the title compound (2.14 g, 96%). LC-MS: $t_R$=1.26 min.

[2-(4-Chloro-3-hydroxymethyl-phenyl)-ethyl]-cyclopropyl-carbamic acid tert-butyl ester Aq. 1M NaOH (48 mL) was added to a suspension of {2-[3-(tert-butyl-dimethyl-silanyloxymethyl)-4-chloro-phenyl]-ethyl}-cyclopropyl-carbamic acid tert-butyl ester (2.10 g, 4.77 mmol) in MeOH (96 mL). The mixture was heated to reflux for 90 min. The mixture was allowed to cool to rt, and the solvents were partially removed under reduced pressure. The resulting aq. mixture was diluted with water (100 mL), and was extracted with Et$_2$O (3×). The combined org. extracts were dried over MgSO$_4$, filtered, and the solvents were removed under reduced pressure. Purification of the crude by FC (EtOAc/heptane 40:60) yielded the title compound (1.34 g, 86%). LC-MS: t$_R$=0.98 min; ES+: 326.30.

[2-(4-Chloro-3-formyl-phenyl)-ethyl]-cyclopropyl-carbamic acid tert-butyl ester MnO$_2$ (1.97 g, 20.4 mmol) was added to a sol. of [2-(4-chloro-3-hydroxymethyl-phenyl)-ethyl]-cyclopropyl-carbamic acid tert-butyl ester (1.33 g, 4.08 mmol) in CH$_3$CN (41 mL). The mixture was stirred overnight at rt. The mixture was filtered over Celite, and was washed with CH$_3$CN and CH$_2$Cl$_2$. Evaporation of the filtrate under reduced pressure yielded the crude title compound (1.32 g, quantitative yield) that was used further without purification. LC-MS: t$_R$=1.05 min.

[2-(4-Chloro-3-cyclopropylaminomethyl-phenyl)-ethyl]-cyclopropyl-carbamic acid tert-butyl ester A mixture of [2-(4-chloro-3-formyl-phenyl)-ethyl]-cyclopropyl-carbamic acid tert-butyl ester (1.32 g, 4.08 mmol) and cyclopropylamine (0.438 mL, 6.1 mmol) in MeOH (41 mL) was heated to reflux for 4 h. The mixture was allowed to cool to rt, and NaBH$_4$ (232 mg) was added in portions. The mixture was stirred for 1 h, and the solvents were removed under reduced pressure. EtOAc (100 mL) was added, and the mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 95:5) yielded the title compound (883 mg, 59%). LC-MS: t$_R$=0.82 min; ES+: 365.38.

(rac.)-(1R*,5S*)-7-{4-[3-(2-Chloro-3,6-difluoro-phenoxy)-propyl]-phenyl}-3,9-diaza-bicyclo[3.3.1]non-6-ene-3,6,9-tricarboxylic acid 3,9-di-tert-butyl ester 6-ethyl ester (A1)

A mixture of compound F3 (56.0 g, 106 mmol), 2-chloro-3,6-difluorophenol (34.8 g, 211 mmol), azadicarboxylic dipiperidide (53.4 g, 211 mmol) and PBu$_3$ (85%, 83 mL, 317 mmol) in toluene (1.20 L) is heated to reflux under nitrogen for 1 h. The mixture is allowed to cool to rt. The mixture is diluted with EtOAc (2.00 L), and the mixture is washed with aq. 1M NaOH (2×900 mL). The org. extracts are dried over MgSO$_4$, filtered, and the solvents are removed under reduced pressure. Purification of the residue by FC (EtOAc/heptane 1:19→1:1) yields the title compound (67.5 g, 94%). LC-MS: t$_R$=1.24 min; ES+: 617.25.

6-[2-(2,6-Dichloro-4-methyl-phenoxy)-ethoxy]-5',6'-dihydro-2'H-[3,4']bipyridinyl-1',3'-dicarboxylic acid 1'-tert-butyl ester 3'-methyl ester (A2)

BuLi (1.6M in hexane, 39.3 mL, 45.2 mmol) was added to a sol. of 5-bromo-2-[2-(2,6-dichloro-4-methyl-phenoxy)-ethoxy]-pyridine (13.0 g, 34.5 mmol) in THF (700 mL) at −78° C. The mixture was stirred for 1 h at −78° C., and ZnCl$_2$ (0.72M in THF, 78.6 mL, 56.5 mmol) was added. The mixture was allowed to warm up to rt. 4-Trifluoromethanesulfonyloxy-5,6-dihydro-2H-pyridine-1,3-dicarboxylic acid 1-tert-butyl ester 3-methyl ester (WO 2004/002957, 11.0 g, 28.3 mmol) and Pd(PPh$_3$)$_4$ (813 mg, 0.704 mmol) were added. The mixture was stirred for 30 min at 70° C., then overnight at rt. Aq. sat. NH$_4$Cl was added, and the mixture was extracted with EtOAc (2×). The org. extracts were dried over MgSO$_4$, filtered, and the solvents were removed under reduced pressure. Purification of the crude by FC (heptane/EtOAc 9:1→5:5) yielded the title compound (10.7 g, 70%). LC-MS: t$_R$=1.16 min; ES+: 537.33.

(rac.)-(1R*,5S*)-7-{4-[3-(2-Chloro-3,6-difluoro-phenoxy)-propyl]-phenyl}-3,9-diaza-bicyclo[3.3.1]non-7-ene-3,6,9-tricarboxylic acid 3,9-di-tert-butyl ester (B1)

In a 250 mL round-bottom flask equipped with a magnetic stirrer is dissolved compound A1 (4.72 g, 6.97 mmol) in EtOH (100 mL). To this is then added aq. 1M NaOH (50 mL), and the resulting colorless sol. is heated to 80° C. for 14 h. The resulting pale pink sol. is allowed to cool to rt, and carefully acidified to a pH of 1.5. The volatiles are removed in vacuo and the resulting residue is partitioned between EtOAc (300 mL) and water (300 mL). The aq. phase is separated and back-extracted with EtOAc (3×300 mL). The combined org. extracts are then washed with brine (500 mL), decolorized with activated charcoal and dried over MgSO$_4$. Filtration through a bed of Celite and concentration of the colorless filtrate in vacuo affords a white froth. Separation of (rac.)-(1R*,5S*)-7-{4-[3-(2-chloro-3,6-difluoro-phenoxy)-propyl]-phenyl}-3,9-diaza-bicyclo[3.3.1]non-6-ene-3,6,9-tricarboxylic acid 3,9-di-tert-butyl ester [1.01 g, 22%; R$_f$=0.55 (1:1 Hex:EtOAc+1% AcOH)] and the title compound (2.77 g, 61%) can be achieved by way of FC (SiO$_2$, 2:1 hexane:EtOAc+1% AcOH). Residual AcOH can be removed quantitatively by first azeotroping with heptane and then toluene. R$_f$=0.50 (1:1 Hex:EtOAc+1% AcOH); ES−=646.8.

Mixture of the Four Possible Diastereoisomers of 7-{4-[3-(2-chloro-3,6-difluoro-phenoxy)-propyl]-phenyl}-3,9-diaza-bicyclo[3.3.1]nonane-3,6,9-tricarboxylic acid 3,9-di-tert-butyl ester (E1)

In a 250 mL round-bottom flask equipped with a magnetic stirrer is suspended compound B1 (1.17 g, 1.80 mmol) and Pd/C (10% w/w, 1.20 g) in MeOH (100 mL). The resulting suspension is deoxygenated and then flushed with H$_2$ gas for 15 min. Finally, the reaction mixture is vigorously stirred at rt under a static H$_2$ atmosphere maintained with a balloon. After 2 h, quantitative consumption of compound B1 can be discerned. The reaction vessel is then vigorously purged with N$_2$ and the suspension is filtered through a bed of Celite and SiO$_2$. After washing the insolubles with copious quantities of CH$_2$Cl$_2$ and EtOAc, the filtrate is concentrated in vacuo to the title compound as a mixture of four diastereomers (1.116 g, 95% crude yield, ES−=648.9). This material is used further without purification.

(rac.)-(1R*,5S*,6R*,7S*)-7-{4-[3-(2-Chloro-3,6-difluoro-phenoxy)-propyl]-phenyl}-6-[cyclopropyl-(2,3-dichloro-benzyl)-carbamoyl]-3,9-diaza-bicyclo[3.3.1]-nonane-3,9-dicarboxylic acid di-tert-butyl ester (D2) and (rac.)-(1R*,5S*,6R*,7R*)-7-{4-[3-(2-chloro-3,6-difluoro-phenoxy)-propyl]-phenyl}-6-[cyclopropyl-(2,3-dichloro-benzyl)-carbamoyl]-3,9-diaza-bicyclo[3.3.1]-nonane-3,9-dicarboxylic acid di-tert-butyl ester (D1)

In a 100 mL round-bottom flask equipped with a magnetic stirrer is combined compound E1 (905 mg, 1.39 mmol), cyclopropyl-(2,3-dichloro-benzyl)-amine (prepared from 2,3-dichlorobenzaldeyhde and cyclopropylamine by reductive amination, 600 mg, 2.78 mmol), HOBt (282 mg, 2.08 mmol), and DMAP (509 mg, 4.17 mmol) in DMF (10 mL). EDC.HCl (400 mg, 2.08 mmol) is then added and the resulting yellow sol. is stirred at rt, and the reaction progress is tracked with LC-MS. With the progress completely stalled after 56 h at 86% conversion, the reaction mixture is diluted with 150 mL of Et$_2$O and quenched with cold 10% aq. HCl (150 mL). The org. fraction is separated, and the aq. fraction is back-extracted with Et$_2$O (3×100 mL). The combined org. extracts are washed sequentially with aq. 1 M NaOH (100 mL), water (150 mL) and brine (150 mL). Drying over MgSO$_4$, filtration and concentration of the filtrate in vacuo affords a white froth. Further purification by way of column chromatography (SiO$_2$, 1.5:1 hexane:Et$_2$O) affords the title compound (0.8591 g, 73%) as a 16:80:4 mixture of diastereomers.

200 mg of the mixture thus obtained is then dissolved in 10 mL of 95% CH$_3$CN+4.9% H$_2$O+0.1% formic acid. This solution is then injected, in 500 µL fractions, onto an HPLC equipped with a Phenomenex Synes 4µ maxRP 80 angstrom 100×21.20 mm column. Elution, at a rate of 20 mL/min with isocratic 95% CH$_3$CN+4.9% H$_2$O+0.1% formic acid affords two major diastereomers:

Compound D1: t$_R$=5.04 min, ES−=848.1, white froth, 40.0 mg (20% isolated yield)

Compound D2: t$_R$=6.64 min, ES−=848.1, white froth, 140.4 mg (70% isolated yield)

(rac.)-(3R*,4S*)-3-[Cyclopropyl-(2,3-dimethylbenzyl)carbamoyl]-4-{4-[2-(2,6-dichloro-4-methylphenoxy)ethoxy]phenyl}piperidine-1-carboxylic acid tert-butyl ester (D3)

A sol. of compound E2 (90 mg, 0.17 mmol), (2,3-dimethylbenzyl)cyclopropyl-amine (prepared by reductive amination of 2,3-dimethylbenzaldehyde and cyclopropylamine, 90 mg, 0.51 mmol), DMAP (5 mg, 0.04 mmol), DIPEA (0.118 mL, 0.69 mmol), HOBt (29 mg, 0.21 mmol) and EDC.HCl (49 mg, 0.26 mmol) in CH$_2$Cl$_2$ (3 mL) was stirred for 18 h. The mixture was diluted with EtOAc, washed with aq. 1M HCl and brine. The org. phase was dried over MgSO$_4$, filtered, and the solvents were removed under reduced pressure. The title compound was not further purified. LC-MS: t$_R$=1.25 min, ES+=681.37.

(3R,4S)-3-{[5-Chloro-2-(3-methoxypropyl)benzyl]cyclopropylcarbamoyl}-4-{4-[2-(2,6-dichloro-4-methylphenoxy)ethoxy]phenyl}piperidine-1-carboxylic acid tert-butyl ester (D4)

A sol. of compound E3 (0.052 g, 0.10 mmol), [5-chloro-2-(3-methoxypropyl)-benzyl]cyclopropylamine (0.073 g, 0.30 mmol), DMAP (0.003 g, 0.03 mmol), DIPEA (0.068 mL, 0.40 mmol), HOBt (0.017 g, 0.13 mmol) and EDC.HCl (0.029 g, 0.15 mmol) in CH$_2$Cl$_2$ (2 mL) was stirred for 48 h. The mixture was diluted with EtOAc, washed with aq. 1M HCl and brine. The org. phase was dried over MgSO$_4$, filtered, and the solvents were removed under reduced pressure. The title compound was not further purified. LC-MS: t$_R$=1.27 min, ES+=761.44.

(3R,4S)-3-{[2-Chloro-5-(2-methoxy-ethyl)-benzyl]-cyclopropyl-carbamoyl}-4-{4-[2-(2,6-dichloro-4-methyl-phenoxy)-ethoxy]-phenyl}-piperidine-1-carboxylic acid tert-butyl ester (D5)

A mixture of compound E3 (200 mg, 0.383 mmol), [2-chloro-5-(2-methoxy-ethyl)-benzyl]-cyclopropyl-amine (120 mg, 0.473 mmol), HOBt (64.7 mg, 0.479 mmol), DMAP (11.7, 0.096 mmol), DIPEA (0.262 mL, 1.53 mmol), and EDC.HCl (110 mg, 0.574 mmol) in CH$_2$Cl$_2$ (4 mL) was stirred for 48 h at rt. The mixture was filtered through Isolute® pre-washed with aq. 1M HCl. The org. layer was dried over MgSO$_4$, filtered, and the solvents were removed under reduced pressure. Purification by FC (EtOAc) yielded the title compound (280 mg, 98%). LC-MS: t$_R$=1.26 min, ES+=747.54.

(rac.)-(3R*,4S*)-3'-{[2-Chloro-5-(3-methoxy-propyl)-benzyl]-cyclopropyl-carbamoyl}-6-[2-(2,6-dichloro-4-methyl-phenoxy)-ethoxy]-3',4',5',6'-tetrahydro-2'H-[3,4']bipyridinyl-1'-carboxylic acid tert-butyl ester (D6)

A mixture of compound E4 (1.00 g, 1.90 mmol), [5-chloro-2-(3-methoxypropyl)-benzyl]cyclopropylamine (531 mg, 2.09 mmol), DIPEA (1.30 mL, 7.61 mmol), DMAP (58.1 mg, 0.476 mmol), HOBt (321 mg, 2.38 mmol) and EDC.HCl (547 mg, 2.86 mmol) in CH$_2$Cl$_2$ (4 mL) was stirred for 4 days at rt. EDC.HCl (100 mg, 0.506 mmol) was added again, and the mixture was stirred for 24 h. CH$_2$Cl$_2$ was added, and the mixture was washed with aq. 1M HCl (1×), water (1×), and brine (1×). The org. layer was dried over MgSO$_4$, filtered, and the solvents were removed under reduced pressure. Purification of the crude by FC (CH$_2$Cl$_2$→CH$_2$Cl$_2$/MeOH 97:3) yielded the title compound (1.14 g, 79%). LC-MS: t$_R$=1.26 min, ES+762.50.

(rac.)-(3R*,4S*)-3'-{[2-Chloro-5-(2-methoxy-ethyl)-benzyl]-cyclopropyl-carbamoyl}-6-[2-(2,6-dichloro-4-methyl-phenoxy)-ethoxy]-3',4',5',6'-tetrahydro-2'H-[3,4']bipyridinyl-1'-carboxylic acid tert-butyl ester (D7)

A mixture of compound E4 (1.00 g, 1.90 mmol), [5-chloro-2-(3-methoxyethyl)-benzyl]cyclopropylamine (533 mg, 2.09 mmol), DIPEA (1.30 mL, 7.61 mmol), DMAP (58.1 mg, 0.476 mmol), HOBt (321 mg, 2.38 mmol) and EDC.HCl (547 mg, 2.86 mmol) in CH$_2$Cl$_2$ (4 mL) was stirred for 5 days at rt. EDC.HCl (100 mg, 0.506 mmol) was added again, and the mixture was stirred for 24 h. CH$_2$Cl$_2$ was added, and the mixture was washed with aq. 1M HCl (1×), water (1×), and brine (1×). The org. layer was dried over MgSO$_4$, filtered, and the solvents were removed under reduced pressure. Purification of the crude by FC (CH$_2$Cl$_2$→CH$_2$Cl$_2$/MeOH 97:3) yielded the title compound (1.12 g, 79%). LC-MS: t$_R$=1.24 min, ES+=746.16.

(3R,4S)-3-[(5-{[tert-Butoxycarbonyl-(2,2-difluoroethyl)-amino]-methyl}-2-chloro-benzyl)-cyclopropyl-carbamoyl]-4-{4-[2-(2,6-dichloro-4-methyl-phenoxy)-ethoxy]-phenyl}-piperidine-1-carboxylic acid tert-butyl ester (D8)

Prepared according to the general conditions A, from compound E3 and from (4-chloro-3-cyclopropylaminomethyl-benzyl)-(2,2-difluoro-ethyl)-carbamic acid tert-butyl ester. LC-MS: t$_R$=1.28 min, ES+=880.26.

(3R,4S)-3-({2-Chloro-5-[(3,3,3-trifluoro-propionylamino)-methyl]-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D9)

Prepared according to the general conditions A, from compound E3 and from N-(4-chloro-3-cyclopropylaminomethyl-benzyl)-3,3,3-trifluoro-propionamide. LC-MS: t$_R$=1.21 min, ES+=828.20.

(3R,4S)-3-({5-[(tert-Butoxycarbonyl-cyclopropylmethyl-amino)-methyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D10)

Prepared according to the general conditions A, from compound E3 and from (4-chloro-3-cyclopropylaminomethyl-benzyl)-cyclopropylmethyl-carbamic acid tert-butyl ester. LC-MS: $t_R$=1.31 min, ES+=872.31.

(3R,4S)-3-{[5-(Acetylamino-methyl)-2-chloro-benzyl]-cyclopropyl-carbamoyl}-4-{4-[2-(2,6-dichloro-4-methyl-phenoxy)-ethoxy]-phenyl}-piperidine-1-carboxylic acid tert-butyl ester (D11)

Prepared according to the general conditions A, from compound E3 and from (N-(4-chloro-3-cyclopropylaminomethyl-benzyl)-acetamide. LC-MS: $t_R$=1.19 min, ES+=758.22.

(3R,4S)-3-({5-[2-(tert-Butoxycarbonyl-methyl-amino)-ethyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D12)

Prepared according to the general conditions A, from compound E3 and from [2-(4-chloro-3-cyclopropylaminomethyl-phenyl)-ethyl]-methyl-carbamic acid tert-butyl ester. LC-MS: $t_R$=1.29 min, ES+=844.33.

(3R,4S)-3-({5-[(tert-Butoxycarbonyl-methyl-amino)-methyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D13)

Prepared according to the general conditions A, from compound E3 and from (4-chloro-3-cyclopropylaminomethyl-benzyl)-methyl-carbamic acid tert-butyl ester. LC-MS: $t_R$=1.28 min, ES+=832.31.

(3R,4S)-3-({2-Chloro-5-[2-(3,3,3-trifluoro-propionylamino)-ethyl]-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D14)

Prepared according to the general conditions A, from compound E3 and from N-[2-(4-chloro-3-cyclopropylaminomethyl-phenyl)-ethyl]-3,3,3-trifluoro-propionamide. LC-MS: $t_R$=1.22 min, ES+=840.25.

(3R,4S)-3-({5-[2-(tert-Butoxycarbonyl-ethyl-amino)-ethyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D15)

Prepared according to the general conditions A, from compound E3 and from [2-(4-chloro-3-cyclopropylaminomethyl-phenyl)-ethyl]-ethyl-carbamic acid tert-butyl ester. LC-MS: $t_R$=1.30 min.

(3R,4S)-3-{[5-(2-Acetylamino-ethyl)-2-chloro-benzyl]-cyclopropyl-carbamoyl}-4-{4-[2-(2,6-dichloro-4-methyl-phenoxy)-ethoxy]-phenyl}-piperidine-1-carboxylic acid tert-butyl ester (D16)

Prepared according to the general conditions A, from compound E3 and from N-[2-(4-chloro-3-cyclopropylaminomethyl-phenyl)-ethyl]-acetamide. LC-MS: $t_R$=1.22 min, ES+=774.29.

(3R,4S)-3-({5-{[tert-Butoxycarbonyl-(2-fluoro-ethyl)-amino]-methyl}-2-chloro-benzyl)-cyclopropyl-carbamoyl]-4-{4-[2-(2,6-dichloro-4-methyl-phenoxy)-ethoxy]-phenyl}-piperidine-1-carboxylic acid tert-butyl ester (D17)

Prepared according to the general conditions A, from compound E3 and from (4-chloro-3-cyclopropylaminomethyl-benzyl)-(2-fluoro-ethyl)-carbamic acid tert-butyl ester. LC-MS: $t_R$=1.28 min, ES+=864.27.

(3R,4S)-3-({5-[(tert-Butoxycarbonyl-ethyl-amino)-methyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D18)

Prepared according to the general conditions C, from compound E3 and from (4-chloro-3-cyclopropylaminomethyl-benzyl)-ethyl-carbamic acid tert-butyl ester. LC-MS: $t_R$=1.30 min, ES+=846.32.

(3R,4S)-3-({5-[(tert-Butoxycarbonyl-cyclopropyl-amino)-methyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D19)

Prepared according to the general conditions C, from compound E3 and from (4-chloro-3-cyclopropylaminomethyl-benzyl)-cyclopropyl-carbamic acid tert-butyl ester. LC-MS: $t_R$=1.31 min, ES+=856.37.

(3R,4S)-3-({5-[2-(tert-Butoxycarbonyl-cyclopropyl-amino)-ethyl]-2-chloro-benzyl}-cyclopropyl-carbamoyl)-4-{4-[2-(2,6-dichloro-4-methyl-phenoxy)-ethoxy]-phenyl}-piperidine-1-carboxylic acid tert-butyl ester (D20)

Prepared according to the general conditions C, from compound E3 and [2-(4-chloro-3-cyclopropylaminomethyl-phenyl)-ethyl]-cyclopropyl-carbamic acid tert-butyl ester. LC-MS: $t_R$=1.31 min, ES+=872.35.

(rac.)-(3R*,4S*)-4-{4-[2-(2,6-Dichloro-4-methyl-phenoxy)-ethoxy]-phenyl}-piperidine-1,3-dicarboxylic acid 1-tert-butyl ester (E2)

To a sol. of compound L2 (0.15 g, 0.27 mmol) in MeOH (1 mL) was added aq. 1M NaOH (1 mL). The mixture was stirred at 70° C. for 2 h. Water was added, and the mixture was extracted with EtOAc. The org. phase was washed with brine, dried over MgSO$_4$, filtered, and the solvents were removed under reduced pressure. The crude residue was purified on a pad of silica gel to yield the title compound (93 mg, 65%). LC-MS: $t_R$=1.12 min, ES+=524.24.

(3R,4S)-4-{4-[2-(2,6-Dichloro-4-methyl-phenoxy)-ethoxy]-phenyl}-piperidine-1,3-dicarboxylic acid 1-tert-butyl ester (E3)

Compound E2 (4.46 g, 8.5 mmol) was separated using a preparative HPLC equipped with a chiral column as described herein above. An isocratic eluent was applied, consisting of 97% hexane, 3% ethanol, and 0.1% TFA. The title compound was obtained (1.35 g, 30%). Analytical chiral HPLC (same eluent as preparative): $t_R$=29.00 min.

(rac.)-(3R*,4S*)-6-[2-(2,6-Dichloro-4-methyl-phenoxy)-ethoxy]-3',4',5',6'-tetrahydro-2'H-[3,4']bipyridinyl-1',3'-dicarboxylic acid 1'-tert-butyl ester (E4)

A mixture of compound L4 (4.92 g, 9.12 mmol) in aq. 1M NaOH (75 mL) and MeOH (75 mL) was stirred for 4.5 h at 70° C. Aq. 1M HCl was added until a pH of about 4 was reached. The mixture was extracted with EtOAc (3×). The combined org. extracts were washed with brine, dried over MgSO$_4$, filtered, and the solvents were removed under reduced pressure. Drying the residue under high vacuum yielded the crude title compound (4.63 g, 97%) that was used further without purification. LC-MS: $t_R$=1.08 min, ES+: 525.40.

4-{4-[2-(tert-Butyldimethylsilanyloxy)ethoxy]phenyl}-5,6-dihydro-2H-pyridine-1,3-dicarboxylic acid 1-tert-butyl ester 3-methyl ester (F1)

To a sol. of 4-[2-(tert-butyldimethylsilanyloxy)ethoxy] bromobenzene (WO 03/093267, 7.95 g, 24 mmol) in THF (200 mL) at −78° C. was added BuLi (1.6M in hexane, 17.12 mL, 27.4 mmol). The sol. was stirred at −78° C. for 30 min, then ZnCl$_2$ (1M in THF, 30 mL, 30 mmol) was added. The resulting sol. was allowed to warm to rt, and 4-trifluoromethanesulfonyloxy-5,6-dihydro-2H-pyridine-1,3-dicarboxylic acid 1-tert-butyl ester 3-methyl ester (WO 2004/002957, 7.79 g, 20 mmol) in THF (20 mL) and Pd(PPh$_3$)$_4$ (0.69 g, 0.60 mmol) were added. The reaction mixture was heated to 50° C. for 1 h, and stirred 16 h at rt. The mixture was cooled to 0° C., and aq. sat. NH$_4$Cl was added. EtOAc was added, and the org. phase was washed with brine, dried over MgSO$_4$, filtered, and the solvents were removed under reduced pressure. Purification of the residue by FC (EtOAc/heptane 2:8→1:0) yielded the title compound (8.1 g, 82%). LC-MS: $t_R$=1.23 min, ES+: 506.47.

(rac.)-(1R*,5S*)-7-{4-[3-(tert-Butyl-dimethyl-silanyloxy)-propyl]-phenyl}-9-methyl-3,9-diaza-bicyclo[3.3.1]non-6-ene-3,6-dicarboxylic acid 3-tert-butyl ester 6-ethyl ester (F2)

A sol. of [3-(4-bromo-phenyl)-propoxy]-tert-butyl-dimethyl-silane (102.1 g, 310 mmol) in THF (1.50 L) under nitrogen is cooled to −78° C. BuLi (1.5M in hexane, 212 mL, 318 mmol) is added. After 30 min, ZnCl$_2$ (1M in THF, 465 mL, 465 mmol) is added. The mixture is allowed to warm up to rt. (rac.)-(1R*,5S*)-9-Methyl-7-trifluoromethanesulfonyloxy-3,9-diaza-bicyclo[3.3.1]non-6-ene-3,6-dicarboxylic acid 3-tert-butyl ester 6-ethyl ester (83.6 g, 155 mmol) in THF (100 mL) and then Pd(PPh$_3$)$_4$ (4.48 g, 3.87 mmol) are added. The mixture is heated to reflux for 30 min, and allowed to cool to rt. The mixture is diluted with EtOAc and washed with aq. 1M NaOH (1×). The org. extracts are dried over MgSO$_4$, filtered, and the solvents are removed under reduced pressure. Purification of the residue by FC (MeOH/CH$_2$Cl$_2$ 1:49→1:24→3:47→2:23) yields the title compound (88.6 g, virtually quantitative). LC-MS: $t_R$=0.98 min; ES+: 559.24.

(rac.)-(1R*,5S*)-7-[4-(3-Hydroxy-propyl)-phenyl]-3,9-diaza-bicyclo[3.3.1]-non-6-ene-3,6,9-tricarboxylic acid 3,9-di-tert-butyl ester 6-ethyl ester (F3)

Compound F2 (32.0 g, 57.3 mmol) is dissolved in dry 1,2-dichlorethane (590 mL). NaHCO$_3$ (48.2 g, 573 mmol) and 1-chloroethyl chloroformate (62.5 mL, 573 mmol) are added, and the suspension is heated to 80° C. After 3 h the reaction mixture is allowed to cool to rt. The mixture is filtered, and the filtrate is evaporated under reduced pressure. The residue is dried 15 min under high vacuum. The product is diluted with MeOH (400 mL), and the mixture is heated to 50° C. for 20 min. The reaction mixture is allowed to cool to rt, and the solvents are removed under reduced pressure. The yellow solid is dried under high vacuum for 1 h. The solid is dissolved in CH$_2$Cl$_2$ (190 mL), and the sol. is cooled to 0° C. DIPEA (49.1 mL, 287 mmol) and Boc$_2$O (37.5 g, 172 mmol) are added. The mixture is stirred overnight while warming up to rt. The reaction mixture is diluted with CH$_2$Cl$_2$ (110 mL). The org. layer is washed with aq. 1M HCl (2×300 mL), and aq. sat. NaHCO$_3$ (300 mL). The org. layer is dried over MgSO$_4$, filtered, and the solvents are evaporated under reduced pressure. Purification of the residue by FC (CH$_2$Cl$_2$/MeOH 100:0→2:98→5:95) yields the title compound (26.2 g, 86%). LC-MS: $t_R$=1.05 min; ES+: 531.33.

4-{4-[3-(tert-Butyl-dimethyl-silanyloxy)-propyl]-phenyl}-5,6-dihydro-2H-pyridine-1,3-dicarboxylic acid 1-tert-butyl ester (G1)

4-{4-[3-(tert-Butyl-dimethyl-silanyloxy)-propyl]-phenyl}-5,6-dihydro-2H-pyridine-1,3-dicarboxylic acid 1-tert-butyl ester 3-methyl ester (WO 2004/002957, 17.1 g, 35.0 mmol) is dissolved in a mixture of DMSO (300 mL) and THF (100 mL). Aq. NaOH (1M, 70 mL and 2M, 50 mL) is added. The mixture is heated to 50° C. for 7 h, then cooled to 0° C., and water (100 mL) is added. The pH is adjusted to 2 by the addition of aq. HCl (1M, 100 mL), and the reaction mixture is extracted with EtOAc (2×250 mL). The combined org. layers are dried over MgSO$_4$, filtered, and the solvents are removed under reduced pressure. The slightly brown oil is dried under high vacuum (18 g). LC-MS: $t_R$=0.86 min; [M+H]$^+$=362.05.

This crude compound (17.98 g) is dissolved in DMF (300 mL) followed by the addition of imidazole (6.84 g, 97.7 mmol) and TBDMS-Cl (11.1 g, 73.8 mmol). The mixture is stirred at rt for 14 h. Sat. aq. NH$_4$Cl (250 mL) and water (250 mL) are added, and the mixture is extracted with Et$_2$O (2×250 mL). The combined org. layers are dried over MgSO$_4$, filtered, and the solvents are evaporated under reduced pressure. The residue is dissolved in THF (300 mL), and MeOH (125 mL), water (125 mL) and K$_2$CO$_3$ (3.00 g) are added. The mixture is stirred at rt for 10 min. Aq. sat. NH$_4$Cl (250 mL) and water (25 mL) are added, and the mixture is extracted with EtOAc (2×250 mL). The combined org. layers are dried over MgSO$_4$, filtered, and the solvents are evaporated under reduced pressure. Purification of the residue by FC (hexane/EtOAc=4/1 to 1/1) yields the title compound (5.1 g, 32%). LC-MS: $t_R$=1.16 min; ES+=476.35.

4-{4-[3-(tert-Butyl-dimethyl-silanyloxy)-propyl]-phenyl}-3-[cyclopropyl-(3-methoxy-2-methyl-benzyl)-carbamoyl]-3,6-dihydro-2H-pyridine-1-carboxylic acid tert-butyl ester (H1)

Compound G1 (2 g, 4.21 mmol) is dissolved in CH$_2$Cl$_2$ (30 mL), and (1-chloro-2-methyl-propenyl)-dimethyl-amine (618 mg, 4.63 mmol) is added. The mixture is stirred at rt for 5 min, and cyclopropyl-(3-methoxy-2-methyl-benzyl)-amine (prepared by reductive amination from 3-methoxy-2-methylbenzaldehyde, Comins, D. L.; Brown, J. D., *J. Org. Chem.*, 1989, 54, 3730, and cyclopropylamine, 844 mg, 4.42 mmol) and DIPEA (815 mg, 6.32 mmol) are added. The mixture is stirred at rt for 15 min, diluted with $CH_2Cl_2$ (100 mL), and extracted with aq. 10% citric acid (100 mL). The aq. layer is washed with $CH_2Cl_2$ (50 mL). The combined org. layers are dried over $MgSO_4$, filtered, and the solvents are evaporated under reduced pressure. Purification of the crude by FC ($CH_2Cl_2$/MeOH 19/1) yields the title compound (3.36 g, quantitative yield). LC-MS: $t_R$=1.28 min; ES+=649.42.

4-{4-[3-(tert-Butyl-dimethyl-silanyloxy)-propyl]-phenyl}-3-[cyclopropyl-(2,3-dimethyl-benzyl)-carbamoyl]-3,6-dihydro-2H-pyridine-1-carboxylic acid tert-butyl ester (H2)

By the same procedure as for compound H1, but using cyclopropyl-(2,3-dimethyl-benzyl)-amine (prepared by reductive amination of 2,3-dimethylbenzaldehyde and cyclopropyl amine), instead of cyclopropyl-(3-methoxy-2-methyl-benzyl)-amine, compound H2 (2.84 g, quantitative yield) is prepared from compound G1 (2.00 g). LC-MS: $t_R$=1.30 min; ES+=633.45.

4-{4-[3-(tert-Butyl-dimethyl-silanyloxy)-propyl]-phenyl}-3-[cyclopropyl-(3-methoxy-2-methyl-benzyl)-carbamoyl]-piperidine-1-carboxylic acid tert-butyl ester (J1)

Pd/C (10%; 340 mg) is suspended under nitrogen in EtOH (25 mL). A sol. of compound H1 (3.36 g, 5.19 mmol) in EtOH (25 mL) is added. The mixture is put under $H_2$ (3 bar) for 3 h, filtered over Celite, and concentrated in vacuo. The residue is dried under high vacuum to give the title compound (2.20 g, 65%) that is used further without purification. LC-MS: $t_R$=1.31 min; ES+=651.46.

4-{4-[3-(tert-Butyl-dimethyl-silanyloxy)-propyl]-phenyl}-3-[cyclopropyl-(2,3-dimethyl-benzyl)-carbamoyl]-piperidine-1-carboxylic acid tert-butyl ester (J2)

By the same procedure as for compound J1, the title compound (2.42 g, 85%) is obtained from compound H2 (2.84 g, 4.47 mmol). LC-MS: $t_R$=1.32 min; ES+635.47.

3-[Cyclopropyl-(3-methoxy-2-methyl-benzyl)-carbamoyl]-4-[4-(3-hydroxy-propyl)-phenyl]-piperidine-1-carboxylic acid tert-butyl ester (J3)

Compound J1 (2.20 g, 3.38 mmol) is dissolved in THF (50 mL), followed by the addition of TBAF (1.21 g, 3.84 mmol). The reaction mixture is stirred at rt for 2.5 h, diluted with EtOAc (250 mL) and washed with water (200 mL). The org. layer is dried over $MgSO_4$, filtered, and concentrated in vacuo. Purification of the residue by FC (hexane/EtOAc 1/1) yields the title compound (0.91 g, 50%). LC-MS: $t_R$=1.07 min; ES+=537.37.

3-[Cyclopropyl-(2,3-dimethyl-benzyl)-carbamoyl]-4-[4-(3-hydroxy-propyl)-phenyl]-piperidine-1-carboxylic acid tert-butyl ester (J4)

By the same procedure as for compound J3, the title compound (0.91 g, 46%) is obtained from compound J2 (2.42 g). LC-MS: $t_R$=1.08 min; ES+=521.36.

4-{4-[2-(tert-Butyldimethylsilanyloxy)ethoxy] phenyl}piperidine-1,3-dicarboxylic acid 1-tert-butyl ester 3-methyl ester (K1)

Mg (1.40 g, 58 mmol) was added to a sol. of compound F1 (8.10 g, 17 mmol) in MeOH (40 mL) under Ar. The mixture was stirred for 1 h while maintaining the temperature below 30° C. Aq. 1M HCl (115 mL, 115 mmol) was added dropwise and the mixture was stirred for 1 h. The mixture was extracted with EtOAc (2×). The combined org. layers were washed with water, brine, dried over $MgSO_4$, filtered, and the solvents were removed under reduced pressure. Purification of the residue by FC (EtOAc/heptane 2:1) yielded a 2:3 trans/cis mixture of the title compound (7.6 g, 93%). LC-MS: $t_R$=1.23 min, ES+=508.47.

4-[4-(2-Hydroxyethoxy)phenyl]piperidine-1,3-dicarboxylic acid 1-tert-butyl ester 3-methyl ester (K2)

To a sol. of compound K1 (7.60 g, 15.4 mmol) in THF (150 mL) at 0° C. and under Ar was added TBAF (4.86 g, 15.4 mmol). After stirring the mixture for 1 h, aq. sat. $NH_4Cl$ (100 mL) was added, and the reaction mixture was extracted with EtOAc (2×). The org. layer was washed with water, brine, dried over $MgSO_4$, filtered, and the solvents were removed under reduced pressure. Purification of the residue by FC (EtOAc/heptane 2:1→1:0) yielded the title compound (5.06 g, 87%). LC-MS: $t_R$=0.91 min, ES+=380.30.

4-{4-[2-(2,6-Dichloro-4-methylphenoxy)ethoxy] phenyl}piperidine-1,3-dicarboxylic acid 1-tert-butyl ester 3-methyl ester (L1)

A mixture of compound K2 (5.50 g, 15 mmol), 2,6-dichloro-p-cresol (3.08 g, 18 mmol), azodicarboxylic dipiperidide (7.31 g, 29 mmol) and $PBu_3$ (14 mL, 58 mmol) in toluene (150 mL) was heated to 50° C. for 16 h. The mixture was allowed to cool to rt, filtered, and the precipitate was washed with toluene. The filtrate was diluted with EtOAc, and washed with water (2×) and brine. The org. layer was dried over $MgSO_4$, filtered, and the solvents were removed under reduced pressure. Purification of the crude by FC (EtOAc/heptane 0:1→1:9→2:8) yielded the title compound as a colourless oil (7.3 g, 90%). LC-MS: $t_R$=1.18 min, ES+538.34.

(rac.)-(3R*,4S*)-4-{4-[2-(2,6-Dichloro-4-methylphenoxy)ethoxy]phenyl}-piperidine-1,3-dicarboxylic acid 1-tert-butyl ester 3-methyl ester (L2)

To a sol. of compound L1 (0.21 g, 0.38 mmol) in MeOH (2 mL) under Ar was added NaOMe (6 mg, 0.11 mmol). The mixture was stirred for 3 days at 70° C. Water was added, and the mixture was extracted with EtOAc. The org. phase was washed with brine, dried over $MgSO_4$, filtered, and the solvents were removed under reduced pressure. The title compound (150 mg, 72%) was not further purified. LC-MS: $t_R$=1.18 min, ES+=538.32.

Mixture of all possible stereoisomers of 6-[2-(2,6-dichloro-4-methyl-phenoxy)-ethoxy]-3',4',5',6'-tetrahydro-2'H-[3,4']bipyridinyl-1',3'-dicarboxylic acid 1'-tert-butyl ester 3'-methyl ester (L3)

Compound A2 (7.00 g, 13.0 mmol) was dissolved in MeOH (130 mL). Mg (500 mg, 20.6 mmol) was added slowly. The mixture was stirred for 1 h, and Mg (608 mg, 25.0 mmol) was added again. The mixture was stirred 3 h. Aq. 1M HCl was added slowly, and the mixture was stirred 1 h at rt. The solvents were evaporated under reduced pressure, and the mixture was extracted with EtOAc. The org. extracts were dried over MgSO$_4$, filtered, and the solvents were removed under reduced pressure. Drying under high vacuum yielded the raw title compound (4.92 g, 70%). LC-MS: $t_R$=1.16 min, ES+=539.43.

(rac.)-(3R*,4S*)-6-[2-(2,6-Dichloro-4-methyl-phenoxy)-ethoxy]-3',4',5',6'-tetrahydro-2'H-[3,4']bipyridinyl-1',3'-dicarboxylic acid 1'-tert-butyl ester 3'-methyl ester (L4)

A mixture of compound L3 (5.40 g, 10.0 mmol) and MeONa (540 mg, 10.0 mmol) in MeOH (250 mL) was stirred overnight at 70° C. MeONa (54 mg, 1.00 mmol) was added again, and the mixture was stirred for 5 h at 70° C. MeONa (54 mg, 1.00 mmol) was added again, and the mixture was stirred overnight at 70° C. Aq. 1M HCl was added until a pH of 6-7 was reached. The solvents were evaporated under reduced pressure, and the mixture was extracted with EtOAc. The combined org. extracts were washed with water, and with brine. The org. layer was dried over MgSO$_4$, filtered, and the solvents were removed under reduced pressure. Purification of the residue by FC (heptane/EtOAc 8:2 with 1% Et$_3$N) yielded the title compound (4.92 g, 91%). LC-MS: $t_R$=1.16 min, ES+=539.43.

Example 1

(rac.)-(1R*,5S*,6R*,7R*)-7-{4-[3-(2-Chloro-3,6-difluoro-phenoxy)-propyl]-phenyl}-3,9-diaza-bicyclo[3.3.1]nonane-6-carboxylic acid cyclopropyl-(2,3-dichloro-benzyl)-amide In a 25 mL round-bottom flask equipped with a magnetic stirrer is dissolved compound D1 (31 mg, 0.037 mmol) in CH$_2$Cl$_2$ (1 mL). At 0° C., 4M HCl (dioxane, 0.36 mL) is added dropwise and the resulting solution is warmed to rt over 2 h, and then stirred at rt for a further 8 h. The volatiles are then removed in vacuo and the resulting residue is partitioned between CH$_2$Cl$_2$ (10 mL) and aq. 1 M NaOH (10 mL). The org. layer is separated and the aq. wash is back-extracted with CH$_2$Cl$_2$ (3×10 mL). The combined org. extracts are washed with brine (10 mL), dried over MgSO$_4$, filtered, and the filtrate concentrated in vacuo. The crude product thus obtained is purified further by way of column chromatography (SiO$_2$, 95:5 CH$_2$Cl$_2$:2 M NH$_3$ in MeOH) to afford the title compound (15.2 mg, 63%). $t_R$=2.0 min on Agilent Zorbax RX-C18 4.6×150 mm HPLC column (isocratic, 49.8 CH$_3$CN+49.9% H$_2$O+0.1% formic acid); ES+=648.1.

Example 2

(rac.)-(1R*,5S*,6R*,7S*)-7-{4-[3-(2-Chloro-3,6-difluoro-phenoxy)-propyl]-phenyl}-3,9-diaza-bicyclo[3.3.1]nonane-6-carboxylic acid cyclopropyl-(2,3-dichloro-benzyl)-amide In a 25 mL round-bottom flask equipped with a magnetic stirrer is dissolved compound D2 (54 mg, 0.064 mmol) in CH$_2$Cl$_2$ (1 mL). At 0° C., 4M HCl (dioxane, 0.47 mL) is added dropwise and the resulting solution is warmed to rt over 2 h, and then stirred at rt for a further 8 h. The volatiles are then removed in vacuo and the resulting residue is partitioned between CH$_2$Cl$_2$ (10 mL) and aq. 1 M NaOH (10 mL). The org. layer is separated and the aq. wash is back-extracted with CH$_2$Cl$_2$ (3×10 mL). The combined org. extracts are washed with brine (10 mL), dried over MgSO$_4$, filtered and the filtrate concentrated in vacuo. The crude product thus obtained is purified further by way of column chromatography (SiO$_2$, 95:5 CH$_2$Cl$_2$: 2 M NH$_3$ in MeOH) to afford the title compound (36.1 mg, 87%). $t_R$=3.1 min on Agilent Zorbax RX-C18 4.6×150 mm HPLC column (isocratic, 49.8 CH$_3$CN+49.9% H$_2$O+0.1% formic acid); ES+=648.1.

Example 3

4-{4-[3-(2-Chloro-3,6-difluoro-phenoxy)-propyl]-phenyl}-piperidine-3-carboxylic acid cyclopropyl-(3-methoxy-2-methyl-benzyl)-amide The title compound is prepared according to the general procedure described above, from compound J3 and 2-chloro-3,6-difluorophenol. LC-MS: $t_R$=0.99 min; ES+: 583.23.

Example 4

4-{4-[3-(2,6-Dichloro-4-methyl-phenoxy)-propyl]-phenyl}-piperidine-3-carboxylic acid cyclopropyl-(3-methoxy-2-methyl-benzyl)-amide The title compound is prepared according to the general procedure described above, from compound J3 and 2,6-dichloro-p-cresol. LC-MS: $t_R$=1.02 min; ES+: 595.43.

Example 5

4-{4-[3-(2,3,6-Trifluoro-phenoxy)-propyl]-phenyl}-piperidine-3-carboxylic acid cyclopropyl-(3-methoxy-2-methyl-benzyl)-amide The title compound is prepared according to the general procedure described above, from compound J3 and 2,3,6-trifluorophenol. LC-MS: $t_R$=0.98 min; ES+: 567.48.

Example 6

4-{4-[3-(2-Chloro-3,6-difluoro-phenoxy)-propyl]-phenyl}-piperidine-3-carboxylic acid cyclopropyl-(2,3-dimethyl-benzyl)-amide The title compound is prepared according to the general procedure described above, from compound J4 and 2-chloro-3,6-difluorophenol. LC-MS: $t_R$=1.00 min; ES+: 567.26.

Example 7

4-{4-[3-(2,6-Dichloro-4-methyl-phenoxy)-propyl]-phenyl}-piperidine-3-carboxylic acid cyclopropyl-(2,3-dimethyl-benzyl)-amide The title compound is prepared according to the general procedure described above, from compound J4 and 2,6-dichloro-p-cresol. LC-MS: $t_R$=1.04 min; ES+: 579.44.

Example 8

4-{4-[3-(2-Chloro-6-fluoro-3-methyl-phenoxy)-propyl]-phenyl}-piperidine-3-carboxylic acid cyclopropyl-(2,3-dimethyl-benzyl)-amide The title compound is prepared according to the general procedure described above, from compound J4 and 2-chloro-6-fluoro-3-methylphenol. LC-MS: $t_R$=1.04 min; ES+: 563.47.

Example 9

4-{4-[3-(2,3,6-trifluoro-phenoxy)-propyl]-phenyl}-piperidine-3-carboxylic acid cyclopropyl-(2,3-dimethyl-benzyl)-amide The title compound is prepared according to the general procedure described above, from compound J4 and 2,3,6-trifluorophenol. LC-MS: $t_R$=1.00 min; ES+: 551.48.

Example 10

(rac.)-(3R*,4S*)-4-{4-[2-(2,6-Dichloro-4-methylphenoxy)ethoxy]phenyl}-piperidine-3-carboxylic acid cyclopropyl-(2,3-dimethylbenzyl)-amide Compound D3 (0.068 g, 0.10 mmol) was dissolved in $CH_2Cl_2$ (1 mL) and the sol. was cooled to 0° C. 4M HCl in dioxane (1 mL) was added and the reaction mixture was stirred for 1 h at rt. The solvents were evaporated under reduced pressure. Purification of the residue by HPLC yielded the title compound (37 mg, 63%). LC-MS: $t_R$=0.95 min, ES+=581.44.

Example 11

(3R,4S)-4-{4-[2-(2,6-Dichloro-4-methyl-phenoxy)-ethoxy]-phenyl}-piperidine-3-carboxylic acid [2-chloro-5-(3-methoxy-propyl)-benzyl]-cyclopropyl-amide Compound D4 (0.076 g, 0.10 mmol) was dissolved in $CH_2Cl_2$ (1 mL) and the sol. was cooled to 0° C. 4M HCl in dioxane (1 mL) was added and the reaction mixture was stirred for 1 h at rt. Purification of the residue by HPLC yielded the title compound (44 mg, 67%). LC-MS: $t_R$=0.99 min, ES+=661.41.

Example 12

(3R,4S)-4-{4-[2-(2,6-Dichloro-4-methyl-phenoxy)-ethoxy]-phenyl}-piperidine-3-carboxylic acid [2-chloro-5-(2-methoxy-ethyl)-benzyl]-cyclopropyl-amide Compound D5 (279 mg, 0.375 mmol) was dissolved in $CH_2Cl_2$ (3 mL). The sol. was cooled to 0° C., and HCl (4M in dioxane, 1.00 mL) was added. The mixture was stirred at 0° C. for 1 h. HCl (4M in dioxane, 1.00 mL) was added again, and the mixture was stirred for 2 h at rt. HCl (4M in dioxane, 1.00 mL) was added again, and the mixture was stirred for 3 h at rt. Aq. 1M NaOH was added until the mixture was slightly basic. The mixture was filtered over Isolute®. The org. layer was dried over $MgSO_4$, filtered, and the solvents were removed under reduced pressure. Purification of the residue by FC (MeOH/$CH_2Cl_2$ 1:19) yielded the title compound (120 mg, 50%). LC-MS: $t_R$=0.96 min, ES+=645.49.

Example 13

(3R,4S)-6-[2-(2,6-Dichloro-4-methyl-phenoxy)-ethoxy]-1',2',3',4',5',6'-hexahydro-[3,4']bipyridinyl-3'-carboxylic acid [2-chloro-5-(3-methoxy-propyl)-benzyl]-cyclopropyl-amide A sol. of compound D6 (1.14 g, 1.50 mmol) in $CH_2Cl_2$ (4.13 mL) was cooled to 0° C., and HCl (4M in dioxane, 3.75 mL) was added. The mixture was stirred for 3 h at rt, and the solvents were removed under reduced pressure. $CH_2Cl_2$ was added and the mixture was washed with aq. 1M NaOH. The org. layer was dried over $MgSO_4$, filtered, and the solvents were removed under reduced pressure. Purification of the residue by HPLC yielded the racemic title compound (621 mg, 63%). This racemate was separated by HPLC (Regis Whelk, eluent B 75%→30% over 30 min, then isocratic). The title compound was obtained (167 mg, 27%). LC-MS: $t_R$=0.95 min; ES+: 684.49. Chiral HPLC column: $t_R$=17.0 min.

Example 14

(3R,4S)-6-[2-(2,6-Dichloro-4-methyl-phenoxy)-ethoxy]-1',2',3',4',5',6'-hexahydro-[3,4']bipyridinyl-3'-carboxylic acid [2-chloro-5-(2-methoxy-ethyl)-benzyl]-cyclopropyl-amide A sol. of compound D7 (1.12 g, 1.50 mmol) in $CH_2Cl_2$ (4.13 mL) was cooled to 0° C., and HCl (4M in dioxane, 3.75 mL) was added. The mixture was stirred for 3 h at rt, and the solvents were removed under reduced pressure. $CH_2Cl_2$ was added and the mixture was washed with aq. 1M NaOH. The org. layer was dried over $MgSO_4$, filtered, and the solvents were removed under reduced pressure. Purification of the residue by HPLC yielded the racemic title compound (392 mg, 40%). This racemate was separated by HPLC (Regis Whelk, eluent B 75%→30% over 30 min, then isocratic). The title compound was obtained (167 mg, 27%). LC-MS: $t_R$=0.94 min; ES+: 646.50. Chiral HPLC column: $t_R$=17.4 min.

Example 15

(3R,4S)-4-{4-[2-(2,6-Dichloro-4-methyl-phenoxy)-ethoxy]-phenyl}-piperidine-3-carboxylic acid {2-chloro-5-[(2,2-difluoro-ethylamino)-methyl]-benzyl}-cyclopropyl-amide Prepared according to the general conditions B, from compound D8, the title compound was obtained (17.8 mg, 26% over two steps). LC-MS: $t_R$=0.83 min; ES+: 682.21.

Example 16

(3R,4S)-4-{4-[2-(2,6-Dichloro-4-methyl-phenoxy)-ethoxy]-phenyl}-piperidine-3-carboxylic acid {2-chloro-5-[(3,3,3-trifluoro-propionylamino)-methyl]-benzyl}-cyclopropyl-amide Prepared according to the general conditions B, from compound D9, the title compound was obtained (30.0 mg, 42% over two steps). LC-MS: $t_R$=0.95 min; ES+: 727.81.

Example 17

(3R,4S)-4-{4-[2-(2,6-Dichloro-4-methyl-phenoxy)-ethoxy]-phenyl}-piperidine-3-carboxylic acid {2-chloro-5-[(cyclopropylmethyl-amino)-methyl]-benzyl}-cyclopropyl-amide Prepared according to the general conditions B, from compound D10, the title compound was obtained (20.3 mg, 30% over two steps). LC-MS: $t_R$=0.84 min; ES+: 672.30.

Example 18

(3R,4S)-4-{4-[2-(2,6-Dichloro-4-methyl-phenoxy)-ethoxy]-phenyl}-piperidine-3-carboxylic acid [5-(acetylamino-methyl)-2-chloro-benzyl]-cyclopropyl-amide Prepared according to the general conditions B, from compound D11, the title compound was obtained (30 mg, 46% over two steps). LC-MS: $t_R$=0.91 min; ES+: 658.25.

Example 19

(3R,4S)-4-{4-[2-(2,6-Dichloro-4-methyl-phenoxy)-ethoxy]-phenyl}-piperidine-3-carboxylic acid [2-chloro-5-(2-methylamino-ethyl)-benzyl]-cyclopropyl-amide Prepared according to the general conditions B, from compound D12, the title compound was obtained (34.3 mg, 53% over two steps). LC-MS: $t_R$=0.82 min; ES+: 646.25.

Example 20

(3R,4S)-4-{4-[2-(2,6-Dichloro-4-methyl-phenoxy)-ethoxy]-phenyl}-piperidine-3-carboxylic acid (2-chloro-5-methylaminomethyl-benzyl)-cyclopropyl-amide Prepared according to the general conditions B, from compound D13, the title compound was obtained (24.1 mg, 38% over two steps). LC-MS: $t_R$=0.81 min; ES+: 630.26.

Example 21

(3R,4S)-4-{4-[2-(2,6-Dichloro-4-methyl-phenoxy)-ethoxy]-phenyl}-piperidine-3-carboxylic acid {2-chloro-5-[2-(3,3,3-trifluoro-propionylamino)-ethyl]-benzyl}-cyclopropyl-amide Prepared according to the general conditions B, from compound D14, the title compound was obtained (30.0 mg, 40% over two steps). LC-MS: $t_R$=0.96 min; ES+: 742.24.

Example 22

(3R,4S)-4-{4-[2-(2,6-Dichloro-4-methyl-phenoxy)-ethoxy]-phenyl}-piperidine-3-carboxylic acid [2-chloro-5-(2-ethylamino-ethyl)-benzyl]-cyclopropyl-amide Prepared according to the general conditions B, from compound D15, the title compound was obtained (11.8 mg, 18% over two steps). LC-MS: $t_R$=0.83 min; ES+: 660.28.

Example 23

(3R,4S)-4-{4-[2-(2,6-Dichloro-4-methyl-phenoxy)-ethoxy]-phenyl}-piperidine-3-carboxylic acid [5-(2-acetylamino-ethyl)-2-chloro-benzyl]-cyclopropyl-amide Prepared according to the general conditions B, from compound D16, the title compound was obtained (11.8 mg, 18% over two steps). LC-MS: $t_R$=0.93 min; ES+: 672.27.

Example 24

(3R,4S)-4-{4-[2-(2,6-Dichloro-4-methyl-phenoxy)-ethoxy]-phenyl}-piperidine-3-carboxylic acid {2-chloro-5-[(2-fluoro-ethylamino)-methyl]-benzyl}-cyclopropyl-amide Prepared according to the general conditions B, from compound D17, the title compound was obtained (21.2 mg, 32% over two steps). LC-MS: $t_R$=0.82 min; ES+: 682.21.

Example 25

(3R,4S)-4-{4-[2-(2,6-Dichloro-4-methyl-phenoxy)-ethoxy]-phenyl}-piperidine-3-carboxylic acid (2-chloro-5-ethylaminomethyl-benzyl)-cyclopropyl-amide Prepared according to the general conditions B, from compound D18, the title compound was obtained (38.7 mg, 60% over two steps). LC-MS: $t_R$=0.81 min; ES+: 644.20.

Example 26

(3R,4S)-4-{4-[2-(2,6-Dichloro-4-methyl-phenoxy)-ethoxy]-phenyl}-piperidine-3-carboxylic acid (2-chloro-5-cyclopropylaminomethyl-benzyl)-cyclopropyl-amide Prepared according to the general conditions B, from compound D19, the title compound was obtained (41.1 mg, 63% over two steps). LC-MS: $t_R$=0.81 min; ES+: 656.24.

Example 27

(3R,4S)-4-{4-[2-(2,6-Dichloro-4-methyl-phenoxy)-ethoxy]-phenyl}-piperidine-3-carboxylic acid [2-chloro-5-(2-cyclopropylamino-ethyl)-benzyl]-cyclopropyl-amide Prepared according to the general conditions B, from compound D20, the title compound was obtained (45.7 mg, 68% over two steps). LC-MS: $t_R$=0.82 min; ES+: 670.24.

Biological Assays

1. Enzyme Immuno Assay (EIA) to Estimate AngI Accumulation and Renin Inhibition 1.1 Preparation of AngI-BSA Conjugate 1.3 mg (1 μmol) of AngI [1-10 (Bachem, H-1680)] and 17 mg (0.26 μmol) of BSA (Fluka, 05475) were dissolved in 4 mL of 0.1M phosphate buffer, pH 7.4, after which 2 mL of a 1:100 dilution of glutaraldehyde in $H_2O$ (Sigma G-5882) was added dropwise. The mixture was incubated overnight at 4° C., then dialyzed against 2 liters of 0.9% NaCl, twice for 4 h at rt, followed by dialysis against 2 liters of PBS 1× overnight at rt. The solution was then filtered with a Syringe filter, 0.45 μm (Nalgene, Cat. No. 194-2545). The conjugate can be stored in polypropylene tubes in 0.05% sodium azide at 4° C. for at least 12 months.

1.2 Preparation of BSA-AngI Coated MTP

Microtiter plates (MPT384, MaxiSorp™, Nunc) were incubated overnight at 4° C. with 80 μl of AngI (1-10)/BSA conjugate, diluted 1:100,000 in PBS 1× in a teflon beaker (exact dilution dependent on batch of conjugate), emptied, filled with 90 μl of blocking solution [0.5% BSA (Sigma A-2153) in PBS 1×, 0.02% $NaN_3$], and incubated for at least 2 h at rt, or overnight at 4° C. 96 well MTP (MaxiSorp™, Nunc) were coated with 200 μl conjugate and blocked with 250 μl blocking solution as above, except that the blocking solution contained 3% BSA. The plates can be stored in blocking solution at 4° C. for 1 month.

1.3 AngI-EIA in 384 well MTP

The AngI (1-10)/BSA coated MTP were washed 3 times with wash buffer (PBS 1×, 0.01% Tween 20) and filled with 75 μl of primary antibody solution (anti-AngI antiserum, pre-diluted 1:10 in horse serum), diluted to a final concentration of 1:100,000 in assay buffer (PBS 1×, 1 mM EDTA, 0.1% BSA, pH 7.4). 5 μl of the renin reaction (or standards in assay buffer) (see below) were added to the primary antibody solution and the plates were incubated overnight at 4° C. After the incubation the plates were washed 3 times with wash buffer and incubated with secondary antibody [anti-rabbit IgG, linked to horseradish peroxidase (Amersham Bioscience, NA 934V), diluted 1:2,000 in wash buffer] for 2 h at rt. The plates were washed 3 times with wash buffer and then incubated for 1 h at rt with substrate solution [1.89 mM ABTS (2.2'-azino-di-(3-ethyl-benzthiazolinsulfonate)] (Roche Diagnostics, 102 946) and 2.36 mM $H_2O_2$ [30%, (Fluka, 95300] in substrate buffer (0.1M sodium acetate, 0.05M sodium dihydrogen phosphate, pH 4.2). The OD of the plate was read at 405 nm in a microplate reader (FLUOStar Optima from BMG). The production of AngI during the renin reaction was quantified by comparing the OD of the sample with the OD of a standard curve of AngI(1-10), measured in parallel.

2. Primary Renin Inhibition Assay: $IC_{50}$ in Buffer, 384 well MTP

The renin assay was adapted from an assay described before (Fischli W. et al., *Hypertension*, 1991, 18:22-31) and consists of two steps: in the first step, recombinant human renin is incubated with its substrate (commercial human tetradecapeptide renin substrate) to create the product Angiotensin I (AngI). In the second step, the accumulated AngI is measured by an immunological assay (enzyme immuno assay, EIA). The detailed description of this assay is found below. The EIA is very sensitive and well suited for renin activity measurements in buffer or in plasma. Due to the low concentration of renin used in this assay (2 fmol per assay tube or 10 pM) it is possible to measure inhibitor affinities in this primary assay down to low pM concentration.

2.1 Methodology

Recombinant human renin (3 pg/μl) in assay buffer (PBS 1×, 1 mM EDTA, 0.1% BSA, pH 7.4), human tetradecapeptide (1-14) substrate (Bachem, M-1120) [5 μM in 10 mM HCl], hydroxyquinoline sulfate (Fluka, 55100) [30 mM in $H_2O$] and assay buffer were premixed at 4° C. at a ratio of 100:30:10:145. 47.5 μl per well of this premix was transferred into polypropylene plates (MTP384, Nunc). Test compounds were dissolved and diluted in 100% DMSO and 2.5 μl added to the premix, then incubated at 37° C. for 3 h. At the end of the incubation period, 5 μl of the renin reaction (or standards in assay buffer) were transferred into EIA assays (as described above) and AngI produced by renin was quantified. The percentage of renin inhibition (AngI decrease) was calculated for each concentration of compound and the concentration of renin inhibition was determined that inhibited the enzyme activity by 50% ($IC_{50}$). The compounds of formula (I) exhibit $IC_{50}$ values between 0.1 nM to 300 nM, especially between 1 nM to 30 nM.

Examples of Inhibition:

| Compound of Example No. | $IC_{50}$ values [nM] |
|---|---|
| 1 | 0.65 |
| 2 | 0.19 |
| 10 | 0.31 |
| 13 | 0.17 |
| 16 | 0.23 |
| 21 | 0.50 |
| 24 | 0.38 |

The invention claimed is:
1. A compound of formula (I):

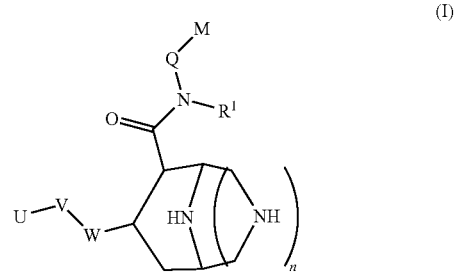

(I)

wherein
W is a six-membered, non benzofused aromatic ring containing one nitrogen atom, wherein said ring is substituted by V in para position;
V represents a bond; —$(CH_2)_r$—; -A-$(CH_2)_s$—; —$CH_2$-A-$(CH_2)_t$—; —$(CH_2)_s$-A-; —$(CH_2)_2$-A-$(CH_2)_u$—; -A-$(CH_2)_v$—B—; —$CH_2$—$CH_2$-$CH_2$-A-$CH_2$—; -A-$CH_2$—$CH_2$—B—$CH_2$—; —$CH_2$-A-$CH_2$—$CH_2$—B—; —$CH_2$—$CH_2$-$CH_2$-A-$CH_2$—$CH_2$—; —$CH_2$—$CH_2$-$CH_2$—$CH_2$-A-$CH_2$—; -A-$CH_2$—$CH_2$—B—$CH_2$—$CH_2$—; —$CH_2$-A-$CH_2$—$CH_2$-B-$CH_2$—; —$CH_2$-A-$CH_2$—$CH_2$-$CH_2$—B—; —$CH_2$—$CH_2$-A-$CH_2$—$CH_2$—B—; —O—$CH_2$—CH($OCH_3$)—$CH_2$—O—; —O—$CH_2$—CH($CH_3$)—$CH_2$—O—; —O—$CH_2$—CH($CF_3$)—$CH_2$—O—; —O—$CH_2$—C($CH_3$)$_2$—$CH_2$-O—; —O—$CH_2$—C($CH_3$)$_2$—O—; —O—C($CH_3$)$_2$—$CH_2$—O—; —O—$CH_2$—CH($CH_3$)—O—; —O—CH($CH_3$)—$CH_2$—O—; —O—$CH_2$—C($CH_2CH_2$)—O—; or —O—C($CH_2CH_2$)—$CH_2$—O—;
A and B independently represent —O— or —S—;
U represents unsubstituted aryl; mono-, di-, tri- or tetra-substituted aryl wherein the substituents are independently selected from the group consisting of halogen, alkyl, alkoxy, and —$CF_3$; or mono-, di-, or tri-substituted heteroaryl wherein the substituents are independently selected from the group consisting of halogen, alkyl, alkoxy, and —$CF_3$;
Q represents methylene or ethylene;
M represents an aryl, quinolinyl, isoquinolinyl, dihydroquinolinyl or tetrahydroquinolinyl group wherein said groups can optionally be mono- or di-substituted with substituents independently selected from the group consisting of alkyl, alkoxy, —$OCF_3$, —$CF_3$, hydroxy-alkyl, halogen, alkyl-O—$(CH_2)_{0-4}$—$CH_2$—, alkyl-O—$(CH_2)_{2-4}$—O—, $R'_2$N—$(CH_2)_{0-4}$—$CH_2$—, and R'''NH—C(=O)—(O)$_{0-1}$—$(CH_2)_{0-4}$—$CH_2$—,
wherein R' is independently selected from the group consisting of hydrogen, alkyl (optionally substituted by one, two or three fluorine atoms), cyclopropyl, cyclopropyl-methyl, —C(=O)O—R", and —C(=O)—R", wherein R" is $C_1$-$C_4$-alkyl, —$CF_3$, —$CH_2$—$CF_3$ or cyclopropyl; and wherein R''' is alkyl or cyclopropyl;

$R^1$ represents cycloalkyl;

n is the integer 0;

r is the integer 3, 4, 5, or 6;

s is the integer 2, 3, 4, or 5;

t is the integer 1, 2, 3, or 4;

u is the integer 1, 2, or 3; and v is the integer 2, 3, or 4;

in free or pharmaceutically acceptable salt form, wherein the configurations at positions 3 and 4 of the piperidine ring of the compound of formula (I) are 3R and 4S, respectively.

2. The compound according to claim 1, wherein M represents an aryl, quinolinyl, isoquinolinyl, dihydroquinolinyl or tetrahydroquinolinyl group, wherein said groups can optionally be mono- or di-substituted with substituents independently selected from the group consisting of alkyl, alkoxy, —$OCF_3$, —$CF_3$, hydroxy-alkyl, halogen, alkyl-O—$(CH_2)_{0-4}$—$CH_2$—, alkyl-O—$(CH_2)_{2-4}$—O—, and $R'_2N$—$(CH_2)_{0-4}$—$CH_3$—, wherein R' is independently selected from the group consisting of hydrogen, alkyl, cyclopropyl, and —C(=O)—R", and wherein R" is $C_1$-$C_4$-alkyl, alkyl, —$CF_3$, —$CH_2$—$CF_3$ or cyclopropyl.

3. The compound according to claim 1, wherein M represents the following radical:

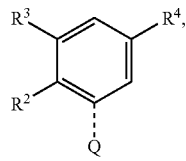

wherein $R^2$ is methyl or chlorine, $R^3$ is hydrogen, and $R^4$ represents hydrogen, —$CH_2CH_2$—O—$CH_3$, —$CH_2CH_2CH_2$—O—$CH_3$, or R'NH—$(CH_2)_{0-1}$—$CH_2$, wherein R' is —$CH_2$—$CHF_2$, —$CH_2$—$CF_3$, cyclopropyl, —CO—$CH_3$, —CO—$CH_2$—$CF_3$, —CO—$CH_2$—$CH_3$, or cyclopropyl-carbonyl, with the proviso that in this case, $R^4$ is hydrogen, $R^3$ represents methyl, methoxy, chlorine, or —O—$CH_2CH_2$—O—$CH_3$.

4. The compound according to claim 1, wherein Q is methylene.

5. The compound according to claim 1, wherein V represents a.) -A-$(CH_2)_s$-, wherein A represents O, wherein s is 2 or 3 and wherein V is linked to U of the compound of formula (I) via A, or b.) —$OCH_2CH_2O$—.

6. The compound according to claim 1, wherein U is a mono-, di-, or tri-substituted phenyl.

7. The compound according to claim 1, wherein $R^1$ is cyclopropyl.

8. The compound according to claim 1, wherein the compound of formula (I) is selected from the group consisting of:

(3R,4S)-6-[2-(2,6-dichloro-4-methyl-phenoxy)-ethoxy]-1',2',3',4',5',6'-hexahydro-[3,4']bipyridinyl-3'-carboxylic acid [2-chloro-5-(3-methoxy-propyl)-benzyl]-cyclopropyl-amide, in free or pharmaceutically acceptable salt form; and (3R,4S)-6-[2-(2,6-dichloro-4-methyl-phenoxy)-ethoxy]-1',2',3',4',5',6'-hexahydro-[3,4']bipyridinyl-3'-carboxylic acid [2-chloro-5-(2-methoxy-ethyl)-benzyl]-cyclopropyl-amide in free or pharmaceutically acceptable salt form.

9. A pharmaceutical composition comprising: the compound according to claim 1 and a pharmaceutically acceptable carrier material.

* * * * *